United States Patent
Juzbasic et al.

(10) Patent No.: US 10,136,969 B2
(45) Date of Patent: Nov. 27, 2018

(54) METHOD AND SYSTEM FOR TOOTH RESTORATION

(71) Applicant: Biodenta Swiss AG, Berneck (CH)

(72) Inventors: Amir Juzbasic, Bethesda, MD (US); Alireza Tavassoli, Gaithersburg, MD (US)

(73) Assignees: Alireza Tavassoli, Brooklyn, NY (US); Amir Juzbasic, Bethesda, MD (US)

( * ) Notice: Subject to any disclaimer, the term of this patent is extended or adjusted under 35 U.S.C. 154(b) by 123 days.

(21) Appl. No.: 14/609,195

(22) Filed: Jan. 29, 2015

(65) Prior Publication Data

US 2015/0230894 A1     Aug. 20, 2015

Related U.S. Application Data

(60) Provisional application No. 61/942,067, filed on Feb. 20, 2014.

(51) Int. Cl.

| | |
|---|---|
| *A61C 5/00* | (2017.01) |
| *A61C 8/00* | (2006.01) |
| *A61C 9/00* | (2006.01) |
| *A61C 13/00* | (2006.01) |
| *A61B 6/14* | (2006.01) |
| *B33Y 80/00* | (2015.01) |

(52) U.S. Cl.
CPC .............. *A61C 8/0095* (2013.01); *A61B 6/14* (2013.01); *A61C 8/0089* (2013.01); *A61C 9/004* (2013.01); *A61C 13/0019* (2013.01); *B33Y 80/00* (2014.12)

(58) Field of Classification Search
CPC ..... A61C 8/0095; A61C 8/0089; A61C 9/004; A61C 13/0004; A61C 13/0019; A61B 6/14; B33Y 80/00
See application file for complete search history.

(56) References Cited

U.S. PATENT DOCUMENTS

| 4,003,707 A | 1/1977 | Lübbers et al. |
|---|---|---|
| 5,675,407 A | 10/1997 | Geng |

(Continued)

FOREIGN PATENT DOCUMENTS

| DE | 102011084111 A1 | 4/2013 |
|---|---|---|
| JP | S51110386 A | 9/1976 |

(Continued)

OTHER PUBLICATIONS

International Search Report issued in corresponding International Application No. PCT/EP2015/053518 dated Aug. 17, 2015.

(Continued)

*Primary Examiner* — Nicholas Lucchesi
(74) *Attorney, Agent, or Firm* — Davis & Bujold PLLC; Michael J. Bujold

(57) ABSTRACT

A method for denture restoration includes steps of generating sets of digital information of a mouth cavity of a person for providing firstly either an orientation appliance or a temporary restoration and subsequently a final restoration. The digital information is generated firstly from the mouth cavity alone and subsequently with the orientation appliance or the temporary restoration within the mouth cavity. The invention also relates to a system for performing this method, and to an orientation appliance and a prosthetic guide to be used in performing the method.

15 Claims, 10 Drawing Sheets

(56) References Cited

U.S. PATENT DOCUMENTS

| | | |
|---|---|---|
| 6,028,672 A | 2/2000 | Geng |
| 6,147,760 A | 11/2000 | Geng |
| 6,345,191 B1 | 2/2002 | Hartmann et al. |
| 7,153,135 B1 | 12/2006 | Thomas |
| 7,474,932 B2 | 1/2009 | Geng |
| 2008/0171305 A1 | 7/2008 | Sonenfeld et al. |
| 2008/0261165 A1* | 10/2008 | Steingart ............ A61C 13/0004 433/24 |
| 2010/0105009 A1 | 4/2010 | Karkar et al. |
| 2011/0111362 A1 | 5/2011 | Haber |
| 2012/0010740 A1 | 1/2012 | Swaelens et al. |
| 2012/0012120 A1 | 1/2012 | Giffey et al. |
| 2012/0015316 A1* | 1/2012 | Sachdeva ................ A61B 1/24 433/24 |
| 2012/0282572 A1* | 11/2012 | MacLeod ........... A61C 13/0004 433/202.1 |
| 2012/0295223 A1 | 11/2012 | Robb et al. |
| 2013/0218532 A1 | 8/2013 | Thompson et al. |

FOREIGN PATENT DOCUMENTS

| | | |
|---|---|---|
| JP | S5774012 U | 5/1982 |
| JP | S5940844 A | 3/1984 |
| JP | H0933532 A | 2/1997 |
| JP | 2000292354 A | 10/2000 |
| JP | 2009125342 A | 6/2009 |
| WO | 2010059692 A2 | 5/2010 |
| WO | 2012083960 A1 | 6/2012 |
| WO | 2013005241 A2 | 1/2013 |
| WO | 2013041382 A1 | 3/2013 |
| WO | 2013108062 A1 | 7/2013 |

OTHER PUBLICATIONS

Japanese Office Action issued in corresponding Japanese Patent Appln. No. 2014-537540, 5 pages.

* cited by examiner

METHOD AND SYSTEM FOR TOOTH RESTORATION

This application claims benefit of provisional application 61/942,067, filed Feb. 20, 2014.

FIELD OF THE INVENTION

The present invention is related to a method and system for tooth restoration, in particular full mouth restoration, as well as to components useful for such a method and system.

BACKGROUND

Tooth restoration, in particular full mouth restoration (i.e. the replacement of all natural teeth by artificial teeth or a denture), is still a time-consuming procedure. According to the conventional procedure, a cast impression of a patient's mandible and/or maxilla has to be made, processed and used for the design and manufacture of a final restoration comprising customized artificial teeth. In said process, the mouth cavity is inspected visually, and according to this visual inspection the locations for implants are selected. Said procedure is complex and dependent on the skills of the persons involved in said procedure.

In particular in the case where a full mouth restoration is needed, e.g. because no natural teeth have remained or the remaining natural teeth are in bad state and need replacement, there is the additional problem of the lack of any reference point in the mouth cavity from which artificial teeth can be designed. Thus, a full mouth restoration either by providing a removable full denture prosthesis or by providing an implant supported prosthesis (where the prosthesis is fixed to implants previously provided in the jaw bones) is still a challenging task.

In recent years, efforts have been made to make individual steps of the entire process of providing tooth restoration more efficient by using modern technology.

In DE 10 2011 084 111 A1, the operation of an articulator (an appliance used for determining the bite of a person, in particular an edentulous person) is supported by a computer by providing position markers on the upper and lower portion of the articulator and determining their correct position with respect to each other.

In U.S. Pat. No. 7,153,135 B1, a disposable denture is provided by laser scanning the oral cavity of a person and creating the denture by stereolithography. However, said method involves the utilization of previously obtained information on the person's oral cavity with remaining teeth in it as a reference point.

In U.S. Pat. No. 7,474,932 B1, the use of computer-aided design (CAD) for generating a virtual 3D model of a dental prosthesis from information collected with a 3D camera is described.

In WO 2010/059692 A2, a method for producing a diagnostic model is described wherein data are collected from an intraoral scan of a person's mouth cavity, said dated are used for providing both a virtual dental model and a dental master model, said dental master model is provided with radiopaque linkable parts, and further information is gathered from both the virtual dental model and the dental master model. The collected information is combined for manufacturing a diagnostic model. The method is provided for diagnostic planning and not suitable for providing a final restoration.

There is still a need for an efficient method for tooth restoration, in particular implant-supported tooth restoration, which is speedy, economically efficient and accurate.

SUMMARY OF THE INVENTION

The above problem is solved by the method and system of the present invention. The present invention efficiently connects all steps of manufacturing tooth restoration with each other by a carefully devised interplay of steps to be performed with a person to be provided with tooth restoration, and steps to be performed in a dental service center. With the method of the present invention, it is possible to provide a person with a full denture prosthesis or an implant supported temporary restoration within a single session, i.e. at the same day. After the necessary healing period, the final restoration can subsequently be provided also in a further single session.

According to a first aspect, the present invention is related to a method for denture restoration, comprising the steps:
  a) generating a first set of digital information of the mouth cavity of a person;
  b) providing either an orientation appliance or a temporary restoration with the aid of said first set of digital information;
  c) generating a second set of digital information of said mouth cavity with said orientation appliance or said temporary restoration being within said mouth cavity,
  d) providing a temporary restoration or a final restoration with the aid of said second set of digital information, if in step c) said orientation appliance is used for generating said second set of digital information,
  e) generating a third set of digital information of said mouth cavity with said temporary restoration provided in step d) being within said mouth cavity, if in step c) said orientation appliance is used for generating said second set of digital information; and
  f) providing a final restoration with the aid of said second or third set of digital information generated with said temporary restoration being within said mouth cavity.

According to said method, digital information related to the mouth cavity of a person is collected and processed for designing an orientation appliance, in the case of full mouth restoration, or a temporary restoration, in the case of partial restoration. Said orientation appliance or temporary restoration is provided to the location of the person and placed in the persons mouth cavity for the collection of further information which is processed for providing a final restoration.

Preferably, the collected information is sent to a dental service center for digital processing and designing.

According to a second aspect, the present invention is related to a system, preferably for performing a method according to the first aspect, comprising
  at least one device for digital generating information related to a mouth cavity of a person,
  at least one processing unit for performing operations of processing information obtained from said at least one device for generating information related to a mouth cavity of a person, and for designing, with the aid of said processed information, at least one component selected from the group consisting of an orientation appliance, a guided surgery appliance, a prosthetic guide, a temporary restoration and a final restoration,
  at least one manufacturing unit for providing, based on the design generated by the processing unit, at least one component selected from the group consisting of an orientation appliance, a guided surgery appliance, a prosthetic guide, a temporary restoration and a final restoration, and at least one component selected from the group consisting of an orientation appliance, a guided surgery appliance, a prosthetic guide, and a temporary restoration.

According to the present invention, the various parts of said system do not have to be provided at the same location. According to a preferred embodiment of the present invention, the device for generating information related to a mouth cavity of a person is located at the clinical site where the person is provided with tooth restoration, whereas the processing unit and the manufacturing unit are provided at a dental service center. In said embodiment, the components manufactured in the dental service center are transferred to the clinical site.

According to another embodiment of the present invention, another manufacturing unit is also located at the clinical site.

The system of the present invention preferably comprises a specific customized orientation appliance for collecting information of the mouth cavity of an edentulous person. Thus, according to a third aspect, the present invention is related to an orientation appliance, preferably to be used in the system according to the second aspect, said orientation appliance comprising an upper portion and a lower portion, wherein said upper and lower portion are adapted to the dimensions, size and shape of a mouth cavity of a person, wherein said upper and lower portion are connected via a movable part for adjusting the distance between said upper and lower portion, wherein at least one, preferably both, of said upper and lower portion comprises at least one radiopaque marker, preferably a plurality of radiopaque markers corresponding to the number of implants to be provided, for defining the position of an implant to be provided within the mouth cavity of the person, and wherein at least one of said upper and lower portion, preferably the upper portion, preferably comprises at least one artificial tooth, preferably two artificial teeth which can be moved with respect to each other, said artificial tooth being movably linked to said upper or lower portion.

Said orientation appliance can replace a conventional articulator and is used according to the present invention for collecting information on the function (bite, phonetics) as well as on the esthetic aspects of the final restoration.

The system of the present invention preferably comprises a specific appliance for inserting abutments into implants provided in the mouth cavity of an edentulous person. Thus, according to a fourth aspect, the present invention is related to a prosthetic guide, comprising a body adapted to the dimensions, size and shape of the mouth cavity of a person, and at least one opening, preferably a plurality of openings corresponding to the number of provided implants, adapted for inserting an abutment through the opening into an implant provided in the mouth cavity of the person, and optionally at least one, preferably a plurality of abutments corresponding to the number of provided implants, said at least one abutment being provided in said at least one opening.

BRIEF DESCRIPTION OF THE DRAWINGS

The present invention will now be further explained with reference to non-limiting drawings and examples.

DETAILED DESCRIPTION OF THE INVENTION

Figure 1A:
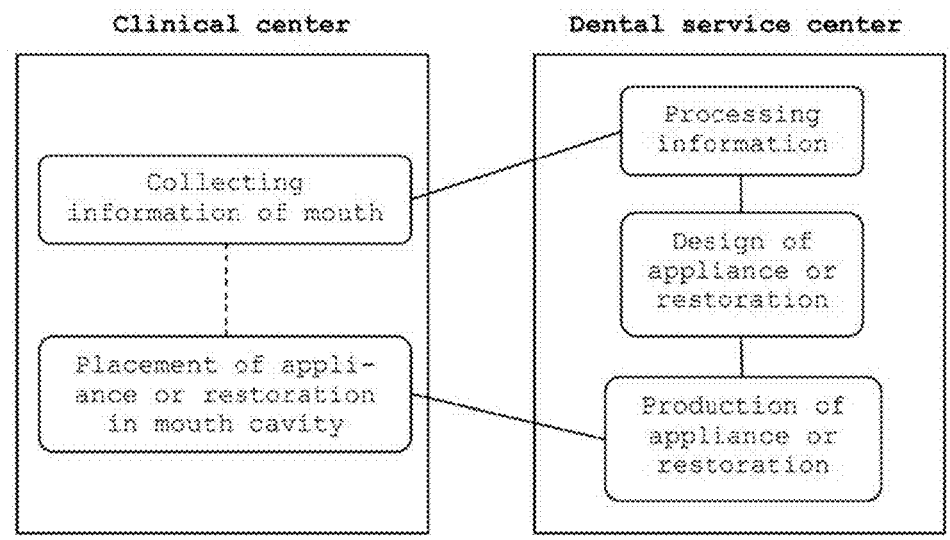
FIG. 1a is a schematic illustration of the DSSC (Dentaswiss service center) concept.

The present invention is related to a method and system for denture restoration. While the present invention is preferably related to full mouth restoration, also partial restoration can be performed with the method and system of the present invention. Both full mouth restoration and partial mouth restoration as described below are covered by the term denture restoration.

According to the present invention, the term "full restoration" or "full mouth restoration" refers to a method where all naturally occurring teeth of a person are replaced by artificial teeth. The artificial teeth may be provided in the form of a removable denture, herein referred to as "full denture edentulous prosthesis". More preferably, the artificial teeth are provided in the form of an implant supported full-edentulous prosthesis.

According to the present invention, the term "designing" is related to the generation of a component, such as a dental appliance, a temporary restoration or a final restoration. Said generation includes the full provision of a three-dimensional shape of said component and is not limited to the provision of two-dimensional drawings. Preferably, according to the present invention the designing step is formed on a processing unit, such as a computer, using design software known in the related field, such as the design software from DentaSwiss.

According to one embodiment of the present invention, the implant supported full-edentulous prosthesis may be a screw-retained prosthesis, i.e. the artificial teeth are retained in respective implants by means of screws normally protruding through the artificial teeth.

According to another embodiment of the present invention, the implant supported full-edentulous prosthesis may be a cement-retained prosthesis, i.e. the artificial teeth are adhered with cement to abutments which themselves are retained in respective implants.

According to the present invention, the term "partial restoration" or "partial mouth restoration" refers to a method where only one or several naturally occurring teeth of a person are replaced by artificial teeth, wherein the artificial teeth are provided in the form of an implant supported partially-edentulous prosthesis. Partial restorations are known in the art and may be provided, for example, in the form of a bridge.

According to one embodiment of the present invention, the implant supported partially-edentulous prosthesis may be a screw-retained prosthesis, i.e. the artificial teeth are retained in respective implants by means of screws normally protruding through the artificial teeth.

According to another embodiment of the present invention, the implant supported partially-edentulous prosthesis may be a cement-retained prosthesis, i.e. the artificial teeth are adhered with cement to abutments which themselves are retained in respective implants.

According to the present invention, the term "temporary restoration" refers to a restoration which is placed into the mouth cavity only for a limited amount of time, usually during a healing period, and which will be subsequently replaced by a final restoration. Temporary restorations are known in the art.

According to the present invention, the term "final restoration" refers to a restoration which is placed into the mouth cavity for an unlimited amount of time, i.e. which is intended as a permanent replacement for one or more artificial teeth. Final restorations are known in the art.

The present invention efficiently connects all steps of manufacturing tooth restoration with each other by a carefully devised interplay of steps to be performed with a person to be provided with tooth restoration, and steps to be performed in a dental service center. This is outlined in FIGS. 1a and 1b.

In FIG. 1a, the so-called Dentaswiss service center concept (DSSC) is illustrated. The person to be provided with a final restoration is located at a clinical center for treatment. The clinical center may be, for example, a dentist's office, a hospital or another location where dental surgery may be carried out.

In the clinical center, information related to the mouth cavity is collected, as will be outlined in more detail below. For said purpose the clinical center is equipped with a device for generating said information, for example with an intraoral scanner (IOS) and/or a cone beam computed tomography device (CBCT).

The thus obtained information is transmitted by usual means (e.g. a cable connection, a network connection, WLAN etc.) to a processing device, such as a computer. According to the DSSC concept, said processing device is located at a dental service center. The dental service center may be, for example, the laboratory of a dental technician, or another location where design and production of dental appliances and temporary and final restorations may be carried out. The dental service center may be at a completely distant location than the clinical center, but may also be situated in the same building, e.g. in a hospital.

According to a preferred embodiment, the dental service center may be a centralized center where a plurality of skilled persons, such as dental technicians, provides their services to a plurality of clinical centers, thus giving rise to synergistic effects. One or several of such centralized centers may be provided.

The dental service center is equipped with processing units, such as computers, for processing the information obtained from the clinical center, and for designing dental appliances and temporary and final restorations. This will be explained in detail below.

According to the DSSC concept, the dental service center is also provided with manufacturing units for producing said dental appliances and temporary and final restorations. The design information generated by the processing unit is transmitted by usual means (e.g. a cable connection, a network connection, WLAN etc.) to such a manufacturing unit, which may be, for example, a 3D printer such as a stereolithographic printer or a CNC (computer numeric controlled) device such as a milling machine.

The thus produced dental appliance or temporary and final restoration is transferred back to the clinical center by usual means such as mail, airmail, or a courier.

In the clinical center, the thus produced dental appliance, or temporary and final restoration is placed into the mouth cavity of the person, and the further steps, if any, discussed in more detail below are performed. For example, as indicated by the broken line in FIG. 1A, further information on the mouth cavity of the person with a dental appliance or temporary restoration in place may be collected and processed in the dental service center as explained above.

Figure 1B:
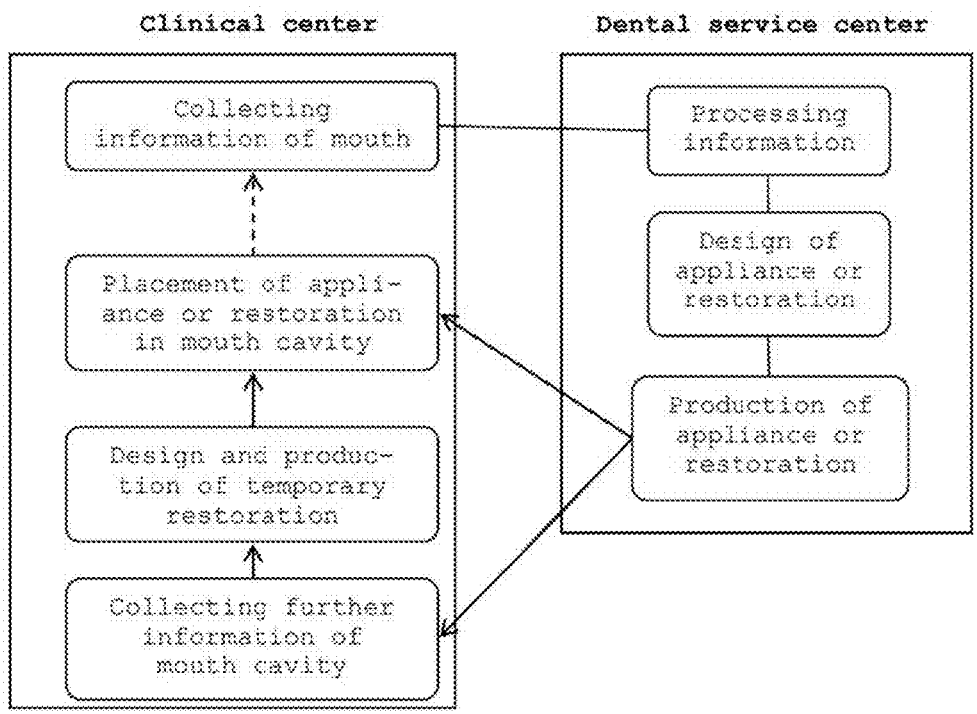
FIG. 1b is a schematic illustration of the DSCS (Dentaswiss clinical center) concept.

In FIG. 1b, the so-called Dentaswiss clinical center concept (DSCS) is illustrated. This concept differs from the DSSC concept in that the clinical center is also provided with equipment for modifying a temporary restoration. In the following, reference is made to the explanations provided with respect to the DSCS concept above, and only the differences thereto are discussed.

In contrast to the DSSC concept, in the DSCS concept, in the clinical center the temporary restoration produced in the dental service center is not immediately placed into its position in the mouth cavity of the person. Rather, after placement of abutments, which will be discussed in more detail below, further information is collected, for example by intraoral scanning preferably with the aid of a scan body. With the aid of said additional information, which will be designated hereinafter as preliminary information, a modification of the design of the temporary restoration may be performed, if necessary or desired.

For said purpose, the clinical center is also equipped with processing units for processing said preliminary information and designing a new temporary restoration, as well as with manufacturing units for producing the newly designed temporary restorations. Those processing units and manufacturing units may preferably be the same kind of units as are provided in the dental service center.

According to a further embodiment, the DSCS concept may be even expanded such that other components such as dental appliances (e.g. the orientation appliance and prosthetic guide described below) may be designed and manufactured at the clinical site.

The newly designed temporary restorations are placed into the mouth cavity of the person, and further method steps as discussed above with respect to FIG. 1A may be performed in the clinical center and/or the dental service center.

In the following, different embodiments of the method of the present invention are described in detail.

Figure 2:
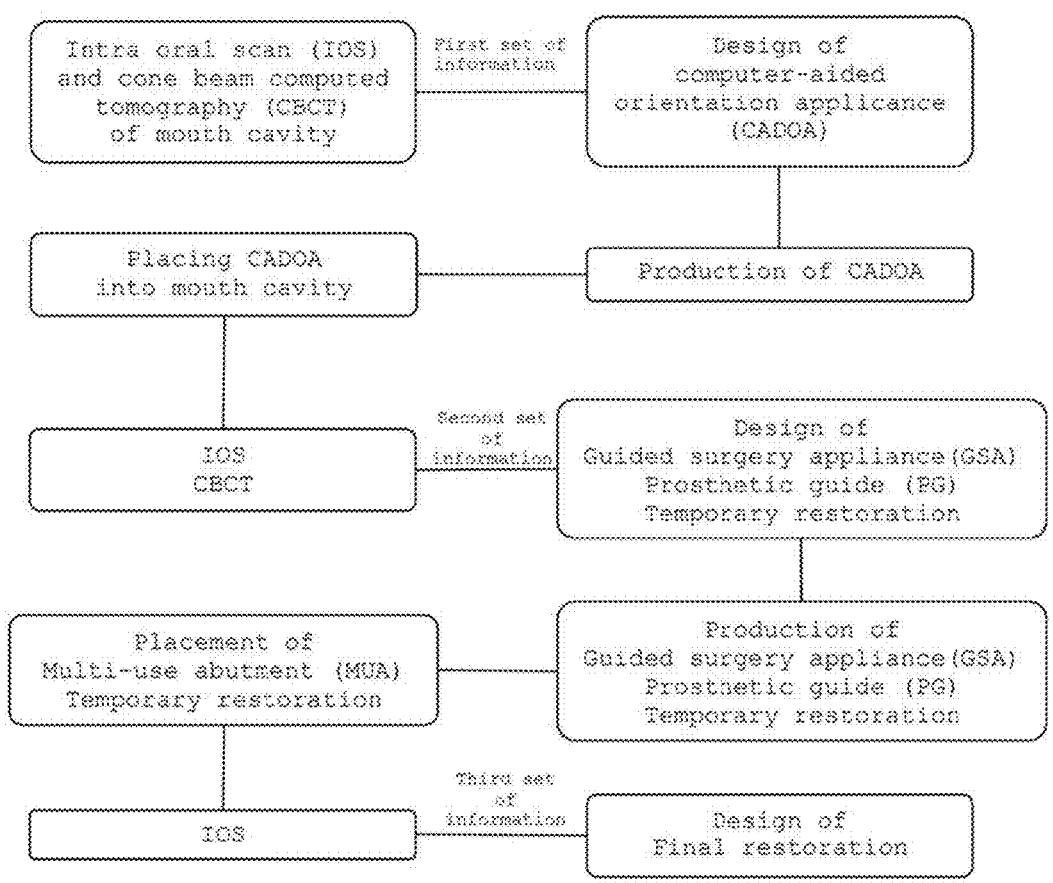
FIG. 2 is a flow-chart of the production of an implant-supported full-edentulous screw-retained prosthesis according to the DSSC (Dentaswiss service center) concept.

In FIG. 2, the manufacture of an implant supported full edentulous screw-retained prosthesis according to the DSSC concept is illustrated. Said method comprises the steps of:

a) generating a first set of digital information of the mouth cavity of a person;
b) providing an orientation appliance with the aid of said first set of digital information;
c) generating a second set of digital information of said mouth cavity with said orientation appliance being within said mouth cavity,
d) providing a temporary restoration with the aid of said second set of digital information,
e) generating a third set of digital information of said mouth cavity with said temporary restoration provided in step d) being within said mouth cavity; and
f) providing a final restoration with the aid of said third set of digital information generated with said temporary restoration being within said mouth cavity.

The person to be provided with a final restoration is located at a clinical center for treatment. The clinical center may be, for example, a dentist's office, a hospital or another location where dental surgery may be carried out.

In the clinical center, information related to the mouth cavity is collected, as will be outlined in more detail below. For said purpose the clinical center is equipped with a device for generating said information, for example with an intraoral scanner (IOS) and/or a cone beam computed tomography device (CBCT).

Intraoral scanning is known in the art. Intraoral scanning can be performed with a camera including any sensor or sensors capable of acquiring image data representative of a person's mouth cavity, in particular its dental dentition. The camera may be a charge-coupled device (CCD) camera or a sensor capable of acquiring different dimensions (e.g., two-dimensional and three-dimensional views) of data representative of a dentition. The camera can include an intra-oral 3D camera (104) configured to acquire 3D surface geometry data representative of the person's dentition. An example of a suitable camera is a 3D Rainbow camera configured to acquire images using techniques described in U.S. Pat. Nos. 5,675,407, 6,028,672, and 6,147,760. Another example is the TRIOS® technology of 3shape, which allows powder-free scanning and on-screen visualization of the digital impression taken.

In addition to the digital impression obtained by intraoral scanning, according to the present invention preferably further information is collected by an X-ray technology. Preferably, the X-ray technology is cone beam computed tomography (CBCT). CBCT is known in the art and is useful for determining anatomical parameters such as bone density and tooth root orientation. According to the present invention, by combining a digital impression technology such as intraoral scanning with a X ray technology such as CBCT, a first set of digital information is generated which is suitable for accurately designing dental appliances and temporary or final restorations.

In a next step, the thus obtained first set of digital information is used for designing an orientation appliance. Preferably, the first set of digital information is transmitted by usual means (e.g. a cable connection, a network connection, WLAN etc.) to a processing device, such as a computer. According to the DSSC concept, said processing device is located at a dental service center. The dental service center may be, for example, the laboratory of a dental technician, or another location where design and production of dental appliances and temporary and final restorations may be carried out. The dental service center may be at a completely distant location than the clinical center, but may also be situated in the same building, e.g. in a hospital.

According to a preferred embodiment, the dental service center may be a centralized center where a plurality of skilled persons, such as dental technicians, provides their services to a plurality of clinical centers, thus giving rise to synergistic effects. One or several of such centralized centers may be provided.

The dental service center is equipped with processing units, such as computers, for processing the information obtained from the clinical center, and for designing dental appliances and temporary and final restorations.

Preferably, the first set of information is transmitted to the processing unit in the form of a DICOM file. DICOM (Digital imaging and communication in medicine) is an open standard for storing and exchanging information in the medicinal area, including image information. DICOM is known in the art and used frequently in medicinal equipment. Providing digital information in the form of a DICOM file thus ensures interoperability between different devices.

As already explained above, full mouth restoration involves the particular problem that in the edentulous mouth there is no reference point (i.e. no remaining natural tooth) from which design of a full prosthesis can be started.

Conventionally, full edentulous prostheses are prepared by using a combination of appliances, such as an articulator and an acrylic tooth set-up. In principle, the method of the present invention can be used in combination with such conventional appliances, in particular for designing a tooth set-up. However, according to a most preferred embodiment and as used in the method of FIG. 2, the first set of information is used for providing the specific orientation appliance of the present invention.

According to the present invention, there is provided an orientation appliance, comprising an upper portion and a lower portion, wherein said upper and lower portion are adapted to the dimensions, size and shape of a mouth cavity of a person,
  wherein said upper and lower portion are connected via a movable part for adjusting the distance between said upper and lower portion,
  wherein at least one of said upper and lower portion comprises at least one radiopaque marker for defining the position of an implant to be provided within the mouth cavity of the person, and
  wherein at least one of said upper and lower portion preferably comprises at least one artificial tooth, said artificial tooth being movably linked to said upper or lower portion.

The orientation appliance of the present invention is a customized product. Its dimensions, size and shape are carefully designed using the first set of information obtained as described above, which is why it is also designated as CADOA (computer-aided designed orientation appliance). It enables to define all important aspects of a final restoration of an edentulous person in advance, in particular by providing the features of a conventional articulator, but in a much more customized and sophisticated form. With the aid of the orientation appliance of the present invention, important parameters such as VOD (vertical dimension of occlusion), centric relation (CR), centric occlusion (CO), esthetic parameters, phonetics and function of the final restoration can be determined.

Figure 8:
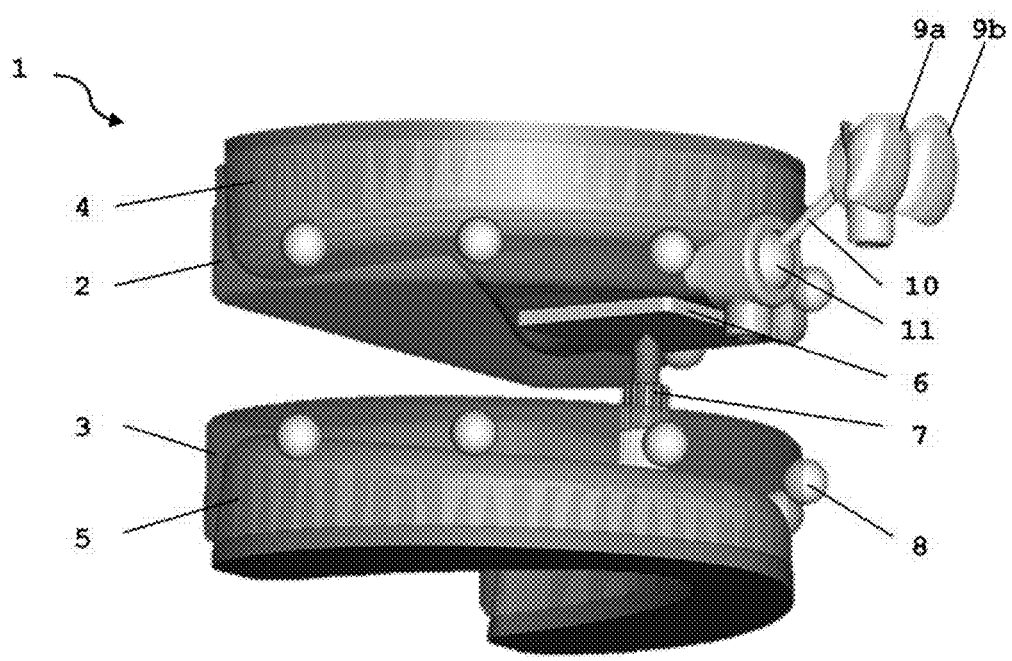
FIG. 8 is a schematic drawing of a preferred embodiment of an orientation appliance according to the present invention.
Figure 9:
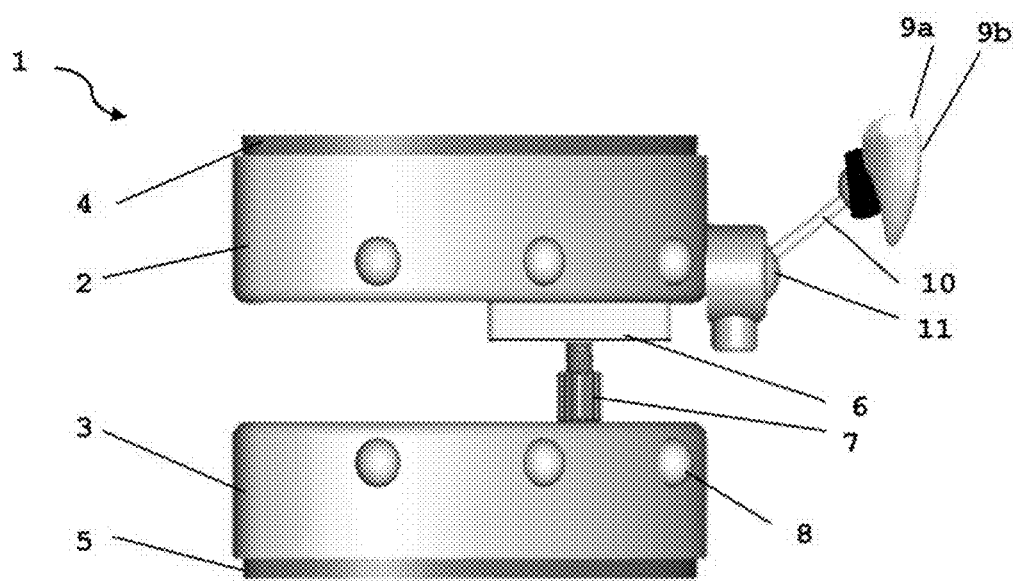
FIG. 9 is a schematic side view of a preferred embodiment of an orientation appliance according to the present invention.

The specific orientation appliance of the present invention will now be explained in more detail with reference to FIGS. 8 and 9, without being limited to the specific embodiment shown in FIGS. 8 and 9.

The orientation appliance (1) comprises an upper portion (2) and a lower portion (3). The upper portion (2) and lower portion (3) surround an upper arch (4) and a lower arch (5), respectively. Said upper arch (4) and lower arch (5) will come into contact with the toothless mucosa of the jaw bones, when the orientation appliance (1) is placed into the mouth cavity.

The upper and lower portion (2,3) and likewise the upper and lower arch (4,5) are adapted to the dimensions, size and shape of the mouth cavity of the person to be provided with a prosthesis, using the first set of information. Thus, it is ensured that the customized orientation appliance accurately fits into the mouth cavity of the person.

The upper portion (2) and the lower portion (3) are connected with each other via a movable part (6,7). Similar to a conventional articulator, with the aid of said movable part (6,7) the distance between the upper portion (2) and the lower portion (3) can be adjusted in order to determine the optimal distance for the upper and lower part of the final restoration.

Generally, any movable part suitable for adjusting the distance between the upper portion (2) and the lower portion (3) of the orientation appliance (1) may be used for the orientation appliance (1) of the present invention. In FIGS. 8 and 9 an embodiment is shown wherein the movable part comprises a plate (6) and a pin (7). The plate (6) is provided at the bottom of the upper portion (2), preferably in a fixed manner. For example, during the manufacture of the upper portion (2), the plate (6) may be embedded into said upper portion (2), or alternatively it may be prepared separately and subsequently adhered to the upper portion (2). The pin (7) may be attached to the lower portion (3) in a similar manner as described with respect to the plate (6) above. By turning the screw-like part of the pin (7), a part within the interior of the pin may be moved out of the pin (7) or back into the pin (7), resulting in a movement of the plate (6) and accordingly of the upper portion (2).

The orientation appliance (1) comprises at least one radiopaque marker (8). The radiopaque marker (8) serves as a reference point in an X-ray scanning method such as CBCT with the orientation appliance being in the mouth cavity of the person. Preferably, the marker (8) is provided at a location at the orientation appliance (1) which corresponds to the position of an implant to be provided, as determined with the first set of information. When the orientation appliance (1) is in the mouth cavity, the marker (8) is thus positioned at a site where an implant is to be provided, allowing an accurate determination of said position during scanning.

The number of markers (8) to be provided at the orientation appliance (1) corresponds to the number of implants to be provided. Depending on the final restoration to be provided, markers (8) may be provided only at the upper portion (2), only at the lower portion (3) or both at the upper and lower portion (2,3). The latter embodiment is the embodiment of choice for the manufacture of full edentulous implant supported prostheses and is shown in FIGS. 8 and 9.

The marker or the plurality of markers (8) is provided at the outer surface of the upper portion (2), only at the lower portion (3) or both at the upper and lower portion (2,3) of the orientation appliance (1). For example, the marker (8) may be embedded into said upper portion (2) and/or lower portion (3), or alternatively it may be prepared separately and subsequently pushed into the upper portion (2) and/or lower portion (3).

The size and form of the marker (8) is defined by the size of the orientation appliance (1), i.e. the marker (8) has to fit into the position alongside the orientation appliance (1) and must not extrude excessively out of the orientation appliance (1). According to the embodiment shown in FIGS. 8 and 9, the marker (8) is in the form of a ball.

The marker (8) is made from a radiopaque material. Any radiopaque material commonly used in dental medicine may be used.

In order to provide a reference point for setting up the teeth of the final restoration, the orientation appliance (1) preferably comprises at least one artificial tooth. Said artificial tooth may be provided either at the upper portion (2), at the lower portion (3) or both at the upper and lower portion (2,3) of the orientation appliance (1). Preferably, as shown in the embodiment in FIGS. 8 and 9, the artificial tooth (9a, 9b) is provided at the front side of the upper portion (2). According to an even more preferred embodiment, two artificial teeth (9a, 9b) are provided at the front side of the upper portion (2).

In order to enable fine adjustment, the artificial tooth or teeth are movably linked to the upper and/or lower portion (2,3). The movable linkage can be realized by any conventional means which allows adjustment of the tooth or teeth in any direction. According to the embodiment of FIGS. 8 and 9, the teeth (9a, 9b) are attached to a rod (10) which itself is provided within a ball bearing (11). This mechanism allows free rotation of the teeth (9a, 9b).

Moreover, the teeth (9a, 9b) are attached to the rod (10) in such a manner that they can be moved towards each other, thus allowing adjustment of a distance between the teeth (9a, 9b).

As described above, the dimensions of the orientation appliance (1), including any part of said orientation appliance (1), are defined by the first set of information collected as described above. Thus, the orientation appliance (1) is designed and subsequently produced in a customized manner, i.e. it fits exactly to the person to be provided with a final restoration. This is achieved using design software known in the related field, such as the design software from DentaSwiss.

The orientation appliance (1) is manufactured by at least one manufacturing unit which is operated according to the design generated by the at least one processing unit. For example, the manufacturing unit may be a CNC (computer numeric controlled) device, such as a CNC milling machine. Alternatively, the manufacturing unit may be a 3D printer, e.g. a stereolithographic printer. It is understood, however, that any other software-controlled manufacturing unit commonly used for said purpose may be equally employed.

The orientation appliance (1) may be made from materials such as polymers as one single piece or in separate pieces which are subsequently connected with each other, as described above. The manufacture of such devices is generally known in the art and need not be discussed in detail here. Thus, the orientation appliance may be provided a single piece or as a kit of parts which can be connected with each other in order to obtain the full orientation appliance.

The thus produced orientation appliance is transferred back to the clinical center by usual means such as mail, airmail, or a courier.

In the clinical center, the orientation appliance is placed into the mouth cavity of the person. The orientation appliance is correctly adjusted within the mouth cavity. In the case of the embodiment of the orientation appliance (1) according to FIGS. 8 and 9, for example the distance between upper portion (2) and lower portion (3) and the position of the teeth (9a, 9b) is adjusted.

After adjustment, in the clinical center, information related to the mouth cavity is collected with the orientation appliance being adjusted within the mouth cavity. Said collection of information is performed as already discussed above with respect to the gathering of the first set of information, preferably by intraoral scanning and additionally by an X-ray technology, preferably cone beam computed tomography (CBCT). According to the present invention, by combining a digital impression technology such as intraoral scanning with a X ray technology such as CBCT, a second set of digital information is generated which is suitable for accurately designing further dental appliances and temporary or final restorations.

Since said second set of information has been collected with the orientation appliance in place in the mouth cavity, it comprises additional valuable information, such as a reference point for setting up teeth as well as information on parameters such as VOD (vertical dimension of occlusion), centric relation (CR), centric occlusion (CO), esthetic parameters, phonetics and function of the final restoration.

Preferably, the second set of digital information is transmitted by usual means (e.g. a cable connection, a network connection or WLAN) to a processing device, such as a computer. According to the DSSC concept, said processing device is located at the dental service center described above.

Preferably, the second set of information is also transmitted to the processing unit in the form of a DICOM file, as described above with respect to the first set of information.

With said second set of information, several different dental appliances as well as a temporary restoration may now be designed and produced. The design and production of those additional components is preferably performed in the same manner as described above for the orientation appliance.

In detail, according to the method of FIG. 2, in said step preferably a guided surgery appliance, a prosthetic guide and a temporary restoration are designed and produced.

A guided surgery appliance is known in the art. It is a tool which enables a dentist to drill boring for implants exactly at the correct location within the mouth cavity. Generally, a guided surgery appliance is a U-shaped body comprising borings at the positions where a dentist has to drill when the guided surgery appliance is in place in the mouth cavity.

In the method of the present invention, a customized guided surgery appliance to fit onto the mucosa of the upper or lower jaw bone of the person to be provided with a prosthesis, is designed and produced with the aid of said second set of information collected as described above. Preferably, said guided surgery appliance is prepared with a 3D printer, e.g. a stereolithographic printer.

It should be explicitly mentioned that the present invention is not related to the step of drilling borings within the jaw bones of a person and providing implants within said borings. The method of the present invention merely provides tools for such an operation, such as the above mentioned guided surgery appliance.

In the method according to FIG. 2, the temporary restoration is supported by implants. According to the present invention, any commonly used implant may be employed. As mentioned above, and outside the scope of this invention, the implants are provided within the mouth cavity with the aid of the above mentioned guided surgery appliance. In a next step, abutments are provided in the implants. Typically, conventionally used abutments such as multi-use abutments (MUA) are screwed into the implants. This can be done in a conventional manner by the dentist without any appliance.

According to a preferred embodiment of the present invention, however, a prosthetic guide is provided as an additional dental appliance.

The prosthetic guide resembles the above described guided surgery appliance. It is designed and manufactured in a similar manner. However, it does not serve as a tool for drilling boring for implants. Rather, it is a tool for aiding the insertion of abutments into implants.

Thus, the present invention is also related to a prosthetic guide, comprising a body adapted to the dimensions, size and shape of the mouth cavity of a person, at least one opening adapted for inserting an abutment through the opening into an implant provided in the mouth cavity of the person, and optionally at least one abutment provided in said opening.

The prosthetic guide is generally a U-shaped body customized to fit onto the mucosa of the upper or lower jaw bone of the person to be provided with a prosthesis. It is designed and produced with the aid of said second set of information collected as described above. Preferably, said prosthetic guide is prepared with a 3D printer, such as a stereolithographic (3D) printer.

The openings of the prosthetic guide are adapted for inserting an abutment through the opening into an implant provided in the mouth cavity of the person. The openings of the prosthetic guide are adapted to the size of the female part of said abutments and thus differ from e.g. the size of drill openings in a conventional drill guide. Preferably, the abutments are inserted into said openings from the bottom side (i.e. the side where the abutments are subsequently moved into the implants). In said embodiment, the openings in the prosthetic guide are not through holes, but are closed at the upper side of the prosthetic guide or at most comprise a tiny hole through which a screwing operation can be performed. Most preferably, the openings in the prosthetic guide may have a conical shape with a diameter extending from a range of 2.0-2.1 mm at the open side to a range of 3.0-3.2 mm at the other end, which as described above is closed or at most comprises a tiny through hole.

The prosthetic guide is preferably provided to the dentist with abutments in the openings, so that the dentist only has to correctly position the prosthetic guide within the mouth cavity and screw the abutments into the implants.

Figure 10:
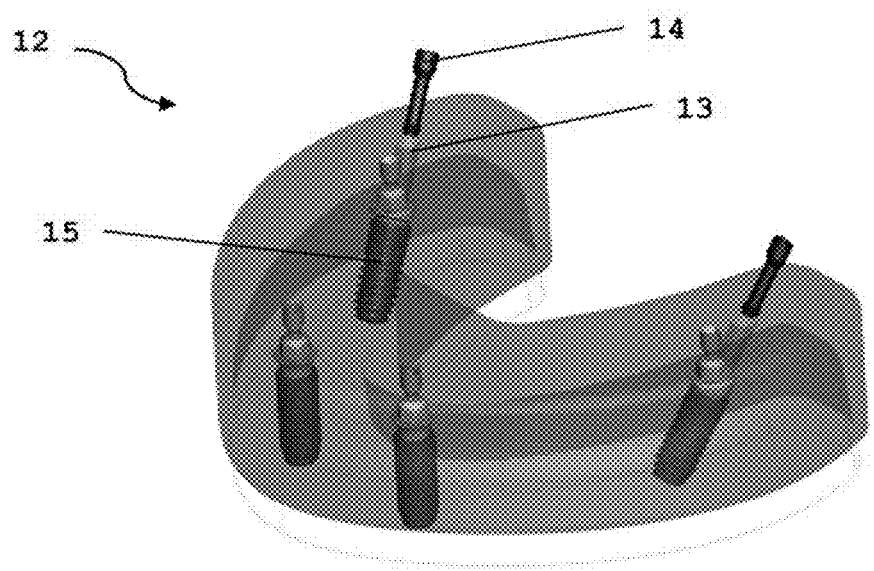
FIG. 10 is a schematic drawing of a preferred embodiment of a prosthetic guide according to the present invention.

An embodiment of a prosthetic guide according to the present invention is shown in FIG. 10. The U-shaped prosthetic guide (12) is provided with one or preferably a plurality of openings (13) corresponding to the number of provided implants. Said openings may be straight or inclined, depending on the position of the implants provided. The size and shape of the openings is customized, i.e. adapted to the dimensions, size and shape of the mouth cavity and to the positions of the implants provided in the mouth cavity.

In FIG. 10, also implants (15) and abutments (14) are shown. The abutments (14) can be inserted into the openings (13). When screwed downwards, the abutments (14) precisely enter the implants (15) due to the accurate design of the openings (13) whose lower end lies over the opening of a respective implant (15). Thus, with the aid of said prosthetic guide (12), a dentist does not have to spend efforts on correctly entering abutments (14) into implants (15), but he simply needs to screw down the abutments (14) provided in the prosthetic guide (12).

The prosthetic guide (12) can be furthermore provided with fixing means, such as additional screws or an adhesive tape, for fixing the prosthetic guide (12) within the mouth cavity.

The thus produced dental appliances are transferred back to the clinical center by usual means such as mail, airmail, or a courier.

In the clinical center, with the aid of the above described guided surgery appliance borings for the implants are drilled and the implants are provided in the mouth cavity in an otherwise conventional manner. Subsequently, with aid of the prosthetic guide abutments are placed into the implants. Optionally, a cap such as a conical sleeve may be placed on the inserted abutments. Finally, the temporary restorations designed and manufactured in the dental service center are provided onto the abutments. Those steps are conventionally performed in dental surgery and not in the scope of the present invention.

The thus provided temporary restoration is allowed to heal, usually for a period of four weeks to three months. It is understood, however, that the healing period may vary from person to person.

After the healing period is finalized, the final restoration is manufactured and placed into the person's mouth cavity. For that purpose, a third set of digital information is obtained from the person's mouth cavity. Said collection of information is performed as already discussed above with respect to the gathering of the first set of information, preferably by intraoral scanning.

According to a preferred embodiment of the present invention, in order to obtain as many information as possible, a sequence of four intraoral scan steps is performed at this stage:

In a first step, the mouth cavity with the provided temporary restorations is scanned.

In a second step, one or more or even all temporary restorations are replaced with scan bodies, and a second intraoral scan is performed. Scan bodies are known in the art and are specifically shaped abutments, whose form resembles the shape of artificial teeth. Thus, the insertion of scan bodies allows the collection of additional information on the placement of artificial teeth, in particular their need for space and the identification of possible interactions between neighboring teeth. An example of a scan body suitable for the present invention is described in WO 2013/041382 A1.

In a third step, an intraoral scan of the left side of the mouth cavity with 50% of temporary restorations in place is performed, i.e. a scan of 50% tissue and 50% temporary restorations is performed.

In a fourth step, an intraoral scan of the right side of the mouth cavity with 50% of temporary restorations in place is performed, i.e. a scan of 50% tissue and 50% temporary restorations is performed.

The thus obtained data are transmitted by usual means (e.g. a cable connection, a network connection, WLAN etc.) to a processing device, such as a computer. According to the DSSC concept, said processing device is located at a dental service center as described above. In said dental service center, a final restoration is designed and manufactured as described above for the other dental appliances and temporary restoration.

The thus produced final restoration is transferred back to the clinical center by usual means such as mail, airmail, or a courier. In the clinical center, the final restoration is placed into the mouth cavity of the person according to a conventional process known in the art. The person is now provided with the desired final restoration.

Figure 3:
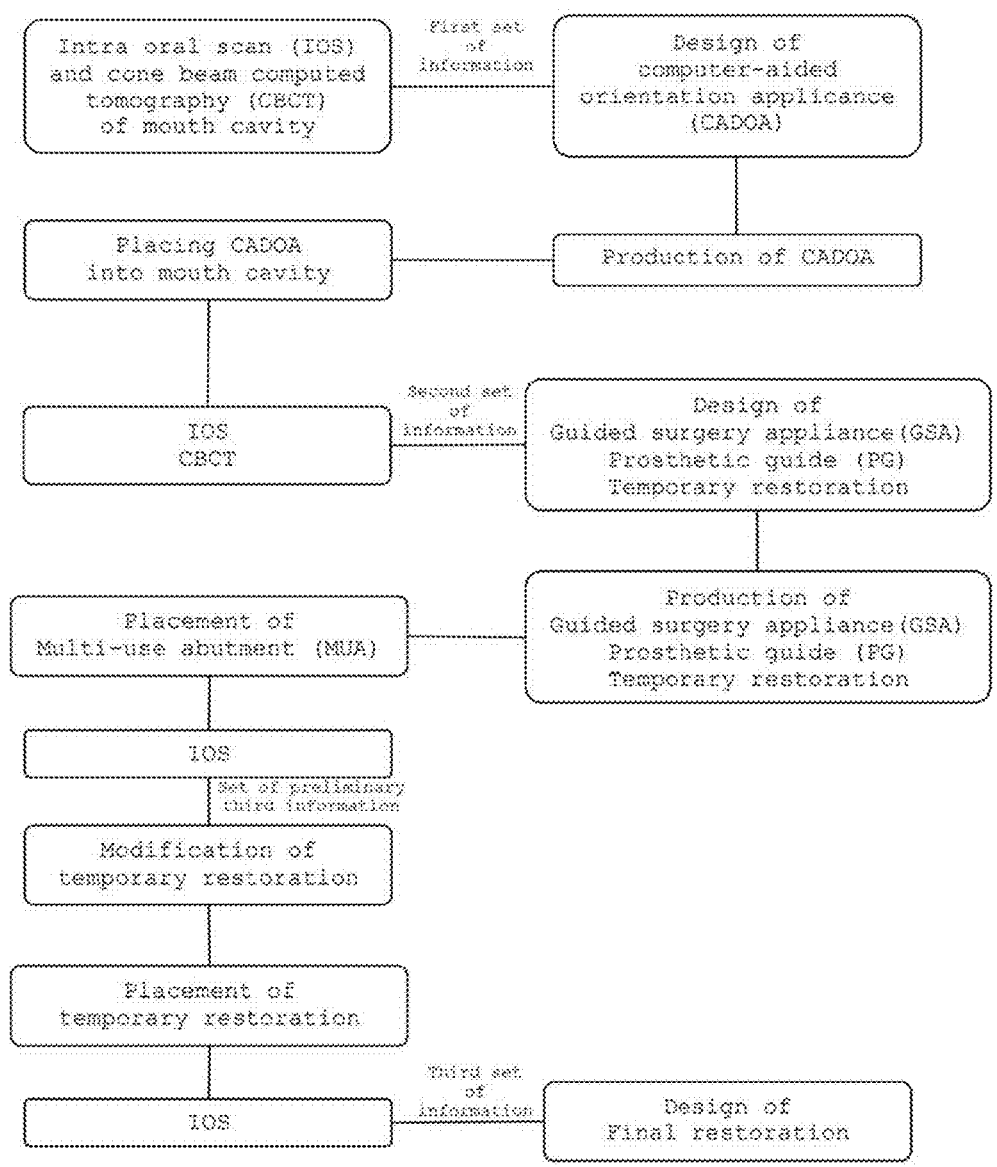
FIG. 3 is a flow-chart of the production of an implant-supported full-edentulous screw-retained prosthesis according to the DSCS (Dentaswiss clinical center) concept.

In FIG. 3, the manufacture of an implant supported full edentulous screw-retained prosthesis according to the DSCS concept is illustrated. Said method comprises the steps of:

a) generating a first set of digital information of the mouth cavity of a person;
b) providing an orientation appliance with the aid of said first set of digital information;
c) generating a second set of digital information of said mouth cavity with said orientation appliance being within said mouth cavity,
d) providing a temporary restoration with the aid of said second set of digital information,
e) generating a set of preliminary third information with at least one abutment, preferably a plurality of abutments corresponding to the number of provided implants, being within said mouth cavity,
f) modifying said temporary restoration with the aid of said set of preliminary third information before being placed into the mouth cavity,
g) generating a third set of digital information of said mouth cavity with said temporary restoration being within said mouth cavity; and
h) providing a final restoration with the aid of said third set of digital information generated with said temporary restoration being within said mouth cavity.

The person to be provided with a final restoration is located at a clinical center for treatment. The clinical center may be, for example, a dentist's office, a hospital or another location where dental surgery may be carried out.

In the clinical center, information related to the mouth cavity is collected, as will be outlined in more detail below. For said purpose the clinical center is equipped with a device for generating said information, for example with an intraoral scanner (IOS) and/or a cone beam computed tomography device (CBCT).

Intraoral scanning is known in the art. Intraoral scanning can be performed with a camera including any sensor or sensors capable of acquiring image data representative of a person's mouth cavity, in particular its dental dentition. The camera may be a charge-coupled device (CCD) camera or a sensor capable of acquiring different dimensions (e.g., two-dimensional and three-dimensional views) of data representative of a dentition. The camera can include an intra-oral 3D camera (104) configured to acquire 3D surface geometry data representative of the person's dentition. An example of a suitable camera is a 3D Rainbow camera configured to acquire images using techniques described in U.S. Pat. Nos. 5,675,407, 6,028,672, and 6,147,760. Another example is the TRIOS® technology of 3shape, which allows powder-free scanning and on-screen visualization of the digital impression taken.

In addition to the digital impression obtained by intraoral scanning, according to the present invention preferably further information is collected by an X-ray technology. Preferably, the X-ray technology is cone beam computed tomography (CBCT). CBCT is known in the art and is useful for determining anatomical parameters such as bone density and tooth root orientation. According to the present invention, by combining a digital impression technology such as intraoral scanning with a X ray technology such as CBCT, a first set of digital information is generated which is suitable for accurately designing dental appliances and temporary or final restorations.

In a next step, the thus obtained first set of digital information is used for designing an orientation appliance. Preferably, the first set of digital information is transmitted by usual means (e.g. a cable connection, a network connection, WLAN etc.) to a processing device, such as a computer. According to the DSCS concept, said processing device is located at a dental service center. The dental service center may be, for example, the laboratory of a dental technician, or another location where design and production of dental appliances and temporary and final restorations may be carried out. The dental service center may be at a completely distant location than the clinical center, but may also be situated in the same building, e.g. in a hospital.

According to a preferred embodiment, the dental service center may be a centralized center where a plurality of skilled persons, such as dental technicians, provides their services to a plurality of clinical centers, thus giving rise to synergistic effects. One or several of such centralized centers may be provided.

The dental service center is equipped with processing units, such as computers, for processing the information obtained from the clinical center, and for designing dental appliances and temporary and final restorations.

Preferably, the first set of information is transmitted to the processing unit in the form of a DICOM file. DICOM (Digital imaging and communication in medicine) is an open standard for storing and exchanging information in the medicinal area, including image information. DICOM is known in the art and used frequently in medicinal equipment. Providing digital information in the form of a DICOM file thus ensures interoperability between different devices.

According to the method described in FIG. 3, in a next step an orientation appliance is designed and provided, as described above with respect to the method of FIG. 2. Preferably, in the method of FIG. 3 an embodiment of an orientation appliance according to FIGS. 8 and 9 is designed, manufactured and used.

As described above, the dimensions of the orientation appliance (1), including any part of said orientation appliance (1), are defined by the first set of information collected as described above. Thus, the orientation appliance (1) is designed and subsequently produced in a customized manner, i.e. it fits exactly to the person to be provided with a final restoration. This is achieved using design software known in the related field, such as the design software from DentaSwiss.

The orientation appliance (1) is manufactured by at least one manufacturing unit which is operated according to the design generated by the at least one processing unit. For example, the manufacturing unit may be a CNC (computer numeric controlled) device, such as a CNC milling machine. Alternatively, the manufacturing unit may be a 3D printer, such as a stereolithographic printer. It is understood, however, that any other software-controlled manufacturing unit commonly used for said purpose may be equally employed.

The orientation appliance (1) may be made from materials such as polymers as one single piece or in separate pieces which are subsequently connected with each other, as described above. The manufacture of such devices is generally known in the art and need not be discussed in detail here.

The thus produced orientation appliance is transferred back to the clinical center by usual means such as mail, airmail, or a courier.

In the clinical center, the orientation appliance is placed into the mouth cavity of the person. The orientation appliance is correctly adjusted within the mouth cavity. In the case of the embodiment of the orientation appliance (1) according to FIGS. 8 and 9, for example the distance between upper portion (2) and lower portion (3) and the position of the teeth (9a, 9b) is adjusted.

After adjustment, in the clinical center, information related to the mouth cavity is collected with the orientation appliance being adjusted within the mouth cavity. Said collection of information is performed as already discussed above with respect to the gathering of the first set of information, preferably by intraoral scanning and additionally by an X-ray technology, preferably cone beam computed tomography (CBCT). According to the present invention, by combining a digital impression technology such as intraoral scanning with a X ray technology such as CBCT, a second set of digital information is generated which is suitable for accurately designing further dental appliances and temporary or final restorations.

Since said second set of information has been collected with the orientation appliance in place in the mouth cavity, it comprises additional valuable information, such as a reference point for setting up teeth as well as information on parameters such as VOD (vertical dimension of occlusion), centric relation (CR), centric occlusion (CO), esthetic parameters, phonetics and function of the final restoration.

Preferably, the second set of digital information is transmitted by usual means (e.g. a cable connection, a network connection or WLAN) to a processing device, such as a computer. According to the DSCS concept, said processing device is located at the dental service center described above.

Preferably, the second set of information is also transmitted to the processing unit in the form of a DICOM file, as described above with respect to the first set of information.

With said second set of information, several different dental appliances as well as a temporary restoration may now be designed and produced. The design and production of those additional components is preferably performed in the same manner as described above for the orientation appliance.

In detail, according to the method of FIG. 3, in said step preferably a guided surgery appliance, a prosthetic guide and a temporary restoration are designed and produced.

A guided surgery appliance has already been described above with respect to the method according to FIG. 2. Reference is made to the respective disclosure above.

In the method of the present invention, a customized guided surgery appliance to fit onto the mucosa of the upper or lower jaw bone of the person to be provided with a prosthesis, is designed and produced with the aid of said second set of information collected as described above. Preferably, said guided surgery appliance is prepared with a stereolithographic (3D) printer.

It should be explicitly mentioned that the present invention is not related to the step of drilling borings within the jaw bones of a person and providing implants within said borings. The method of the present invention merely provides tools for such an operation, such as the above mentioned guided surgery appliance.

In the method according to FIG. 3, the temporary restoration is supported by implants. According to the present invention, any commonly used implant may be employed. As mentioned above, and outside the scope of this invention, the implants are provided within the mouth cavity with the aid of the above mentioned guided surgery appliance. In a next step, abutments are provided in the implants. Typically, conventionally used abutments such as multi-use abutments (MUA) are screwed into the implants. This can be done in a conventional manner by the dentist without any appliance.

According to a preferred embodiment of the present invention, however, a prosthetic guide is provided as an additional dental appliance. A suitable prosthetic guide has already been described above with respect to the method according to FIG. 2. Reference is made to the respective disclosure above. Preferably, an embodiment of a prosthetic guide as shown in FIG. 10 may be used.

The thus produced dental appliances are transferred back to the clinical center by usual means such as mail, airmail, or a courier.

In the clinical center, with the aid of the above described guided surgery appliance borings for the implants are drilled and the implants are provided in the mouth cavity in an otherwise conventional manner. Subsequently, with aid of the prosthetic guide abutments are placed into the implants.

In contrast to the method of FIG. 2, in the method of FIG. 3 according to the DSCS concept a modification of the temporary restoration is performed at the clinical center.

For that purpose, additional information on the mouth cavity is collected. Said additional information is referred to as a set of preliminary third information. According to a preferred embodiment, said set of preliminary third information is obtained by providing one or more scan bodies in the mouth cavity, and an intraoral scan is performed. Scan bodies are known in the art and have already been described above with respect to the method of FIG. 2.

According to the DSCS concept described in FIG. 3, the clinical center is also provided with a processing unit for designing a temporary restoration, as well as with a manufacturing unit for producing a temporary restoration. Suitable processing units and manufacturing units have already been described above with respect to the method of FIG. 2. Reference is made to the disclosure above.

Similar to the design and production of a temporary restoration in a dental service center according to the method of FIG. 2, in the method according to FIG. 3 the pre-designed temporary restoration from the dental service center is now re-designed with the aid of the set of preliminary third information. The re-design is performed at the clinical center with the aid of a processing unit comprising respective software as described above. The re-designed temporary restoration is subsequently produced with a manufacturing unit provided at the clinical center, such as a CNC (computer numeric controlled) device, for example a CNC milling machine, or a 3D printer, such as a stereolithographic printer.

Optionally, a cap such as a conical sleeve may now be placed on the inserted abutments. Finally, the temporary restorations designed and manufactured in the dental service center are provided onto the abutments. Those steps are conventionally performed in dental surgery and not in the scope of the present invention.

The thus provided temporary restoration is allowed to heal, usually for a period of four weeks to three months. It is understood, however, that the healing period may vary from person to person.

After the healing period is finalized, the final restoration is manufactured and placed into the person's mouth cavity. For that purpose, a third set of digital information is obtained from the person's mouth cavity. Said collection of information is performed as already discussed above with respect to the gathering of the first set of information, preferably by intraoral scanning.

According to a preferred embodiment of the present invention, in order to obtain as many information as possible, a sequence of four intraoral scan steps is performed at this stage:

In a first step, the mouth cavity with the provided temporary restorations is scanned.

In a second step, one or more or even all temporary restorations are replaced with scan bodies, and a second intraoral scan is performed. Scan bodies are known in the art and have already been described above with respect to the method according to FIG. 2.

In a third step, an intraoral scan of the left side of the mouth cavity with 50% of temporary restorations in place is performed, i.e. a scan of 50% tissue and 50% temporary restorations is performed.

In a fourth step, an intraoral scan of the right side of the mouth cavity with 50% of temporary restorations in place is performed, i.e. a scan of 50% tissue and 50% temporary restorations is performed.

The thus obtained data are transmitted by usual means (e.g. a cable connection, a network connection, WLAN etc.) to a processing device, such as a computer. According to the DSSC concept, said processing device is located at a dental service center as described above. In said dental service center, a final restoration is designed and manufactured as described above for the other dental appliances and temporary restoration.

The thus produced final restoration is transferred back to the clinical center by usual means such as mail, airmail, or a courier. In the clinical center, the final restoration is placed into the mouth cavity of the person according to a conventional process known in the art. The person is now provided with the desired final restoration.

Figure 4:
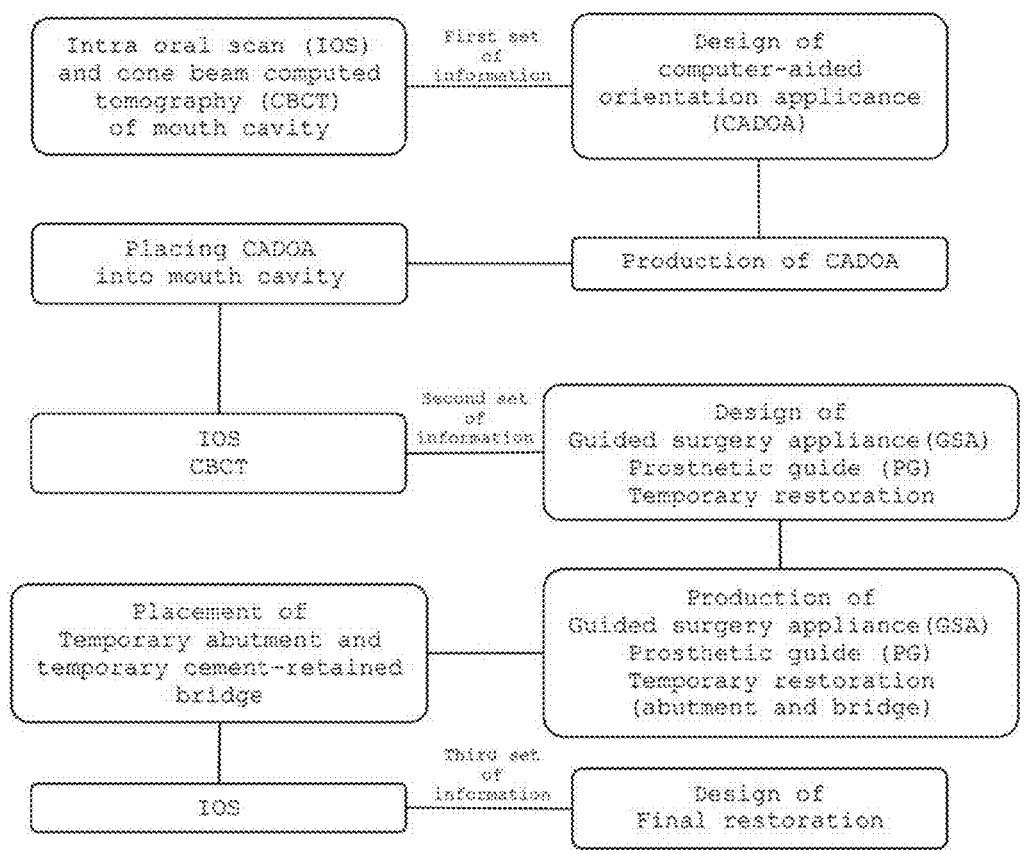
FIG. 4 is a flow-chart of the production of an implant-supported full-edentulous cement-retained prosthesis according to the DSSC (Dentaswiss service center) concept.

The method according to FIG. 4 is similar to the method of FIG. 2. Reference is thus made to the description of the method according to FIG. 2 provided above.

The only difference between the methods of FIGS. 2 and 4 is that in the method of FIG. 2 a screw-retained implant supported prosthesis is provided, whereas in the method of FIG. 4 cement-retained implant supported prosthesis is provided. Thus, in the method of FIG. 4, with the aid of said second set of information a temporary restoration comprising a temporary abutment and a specific temporary restoration such as a bridge are provided.

The one or more temporary abutments are placed into implants previously provided in the mouth cavity, preferably with the aid of a prosthetic guide as described above with respect to the method of FIG. 2. Onto said one or more temporary abutments, by a process commonly known in the art, one or more temporary restorations (e.g. a bridge) are adhered using a cement.

The remaining steps of the method of FIG. 4 are similar to the method of FIG. 2. Reference is thus made to the description of the method according to FIG. 2 provided above.

Next, the provision of partially edentulous screw-retained implant supported prostheses will be described in detail.

Figure 5:
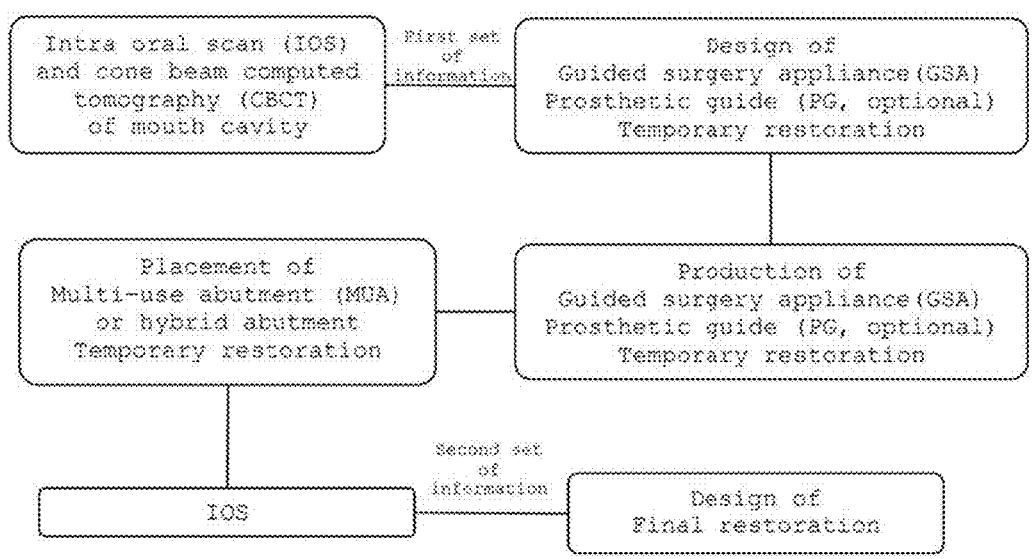
FIG. 5 is a flow-chart of the production of an implant-supported partially edentulous screw-retained prosthesis according to the DSSC (Dentaswiss service center) concept.

In FIG. 5, the manufacture of an implant supported partially edentulous screw-retained prosthesis according to the DSSC concept is illustrated. Said method comprises the steps of:
 a) generating a first set of digital information of the mouth cavity of a person;
 b) providing a temporary restoration with the aid of said first set of digital information,
 c) generating a second set of digital information of said mouth cavity with said temporary restoration being within said mouth cavity; and
 d) providing a final restoration with the aid of said second set of digital information generated with said temporary restoration being within said mouth cavity.

The person to be provided with a final restoration is located at a clinical center for treatment. The clinical center may be, for example, a dentist's office, a hospital or another location where dental surgery may be carried out.

In the clinical center, information related to the mouth cavity is collected, as will be outlined in more detail below. For said purpose the clinical center is equipped with a device for generating said information, for example with an intraoral scanner (IOS) and/or a cone beam computed tomography device (CBCT).

Intraoral scanning is known in the art. Intraoral scanning can be performed with a camera including any sensor or sensors capable of acquiring image data representative of a person's mouth cavity, in particular its dental dentition. The camera may be a charge-coupled device (CCD) camera or a sensor capable of acquiring different dimensions (e.g., two-dimensional and three-dimensional views) of data representative of a dentition. The camera can include an intra-oral 3D camera (104) configured to acquire 3D surface geometry data representative of the person's dentition. An example of a suitable camera is a 3D Rainbow camera configured to acquire images using techniques described in U.S. Pat. Nos. 5,675,407, 6,028,672, and 6,147,760. Another example is the TRIOS® technology of 3shape, which allows powder-free scanning and on-screen visualization of the digital impression taken.

In addition to the digital impression obtained by intraoral scanning, according to the present invention preferably further information is collected by an X-ray technology. Preferably, the X-ray technology is cone beam computed tomography (CBCT). CBCT is known in the art and is useful for determining anatomical parameters such as bone density and tooth root orientation. According to the present invention, by combining a digital impression technology such as intraoral scanning with a X ray technology such as CBCT, a first set of digital information is generated which is suitable for accurately designing dental appliances and temporary or final restorations.

In a next step, the thus obtained first set of digital information is used for designing a temporary restoration and optionally one or more dental appliances. Preferably, the first set of digital information is transmitted by usual means (e.g. a cable connection, a network connection, WLAN etc.) to a processing device, such as a computer. According to the DSSC concept, said processing device is located at a dental service center. The dental service center may be, for example, the laboratory of a dental technician, or another location where design and production of dental appliances and temporary and final restorations may be carried out. The dental service center may be at a completely distant location than the clinical center, but may also be situated in the same building, e.g. in a hospital.

According to a preferred embodiment, the dental service center may be a centralized center where a plurality of skilled persons, such as dental technicians, provides their services to a plurality of clinical centers, thus giving rise to synergistic effects. One or several of such centralized centers may be provided.

The dental service center is equipped with processing units, such as computers, for processing the information obtained from the clinical center, and for designing dental appliances and temporary and final restorations.

Preferably, the first set of information is transmitted to the processing unit in the form of a DICOM file. DICOM (Digital imaging and communication in medicine) is an open standard for storing and exchanging information in the medicinal area, including image information. DICOM is known in the art and used frequently in medicinal equipment. Providing digital information in the form of a DICOM file thus ensures interoperability between different devices.

With said first set of information, several different dental appliances as well as a temporary restoration may now be designed and produced. The design and production of those additional components is preferably performed in the same manner as described above with respect to the method of FIG. 2. Reference is made to the respective disclosure.

In detail, according to the method of FIG. 5, in said step preferably a guided surgery appliance, an optional prosthetic guide and a temporary restoration are designed and produced.

A guided surgery appliance has already been described above with respect to the method according to FIG. 2. Reference is made to the respective disclosure above.

In the method of the present invention, a customized guided surgery appliance to fit onto the mucosa of the upper or lower jaw bone of the person to be provided with a prosthesis, is designed and produced with the aid of said second set of information collected as described above. Preferably, said guided surgery appliance is prepared with a 3D printer, such as a stereolithographic (printer.

It should be explicitly mentioned that the present invention is not related to the step of drilling borings within the jaw bones of a person and providing implants within said borings. The method of the present invention merely provides tools for such an operation, such as the above mentioned guided surgery appliance.

In the method according to FIG. 5, the temporary restoration is supported by implants. According to the present invention, any commonly used implant may be employed. As mentioned above, and outside the scope of this invention, the implants are provided within the mouth cavity with the aid of the above mentioned guided surgery appliance. In an optional next step, abutments may be provided in the implants. Typically, conventionally used abutments such as multi-use abutments (MUA) are screwed into the implants. This can be done in a conventional manner by the dentist without any appliance.

According to a preferred embodiment of the present invention, however, a prosthetic guide is provided as an additional dental appliance. A suitable prosthetic guide has already been described above with respect to the method according to FIG. 2. Reference is made to the respective disclosure above. Preferably, an embodiment of a prosthetic guide as shown in FIG. 10 may be used.

The thus produced dental appliances are transferred back to the clinical center by usual means such as mail, airmail, or a courier.

In the clinical center, with the aid of the above described guided surgery appliance borings for the implants are drilled and the implants are provided in the mouth cavity in an otherwise conventional manner. Subsequently, optionally with the aid of the prosthetic guide abutments are placed into the implants.

Optionally, a cap such as a conical sleeve may now be placed on the inserted abutments. Finally, the temporary restorations designed and manufactured in the dental service center are provided onto the abutments. Those steps are conventionally performed in dental surgery and not in the scope of the present invention.

According to an alternative embodiment of the method of FIG. 5, instead of a multi-use abutment (MUA) also a so called hybrid abutment may be provided in the implants, in the same manner as described above for the MUA. Hybrid abutment are conventionally known in the art and not discussed in detail here. For the insertion of hybrid abutments, the above described prosthetic guide is not necessary and can thus be omitted. The temporary restorations designed and manufactured in the dental service center are provided onto the hybrid abutments, according to this alternative embodiment.

The thus provided temporary restoration is allowed to heal, usually for a period of four weeks to three months. It is understood, however, that the healing period may vary from person to person.

After the healing period is finalized, the final restoration is manufactured and placed into the person's mouth cavity. For that purpose, a second set of digital information is obtained from the person's mouth cavity. Said collection of information is performed as already discussed above with respect to the gathering of the first set of information, preferably by intraoral scanning.

According to a preferred embodiment of the present invention, in order to obtain as many information as possible, a sequence of four intraoral scan steps is performed at this stage:

In a first step, the mouth cavity with the provided temporary restorations is scanned.

In a second step, one or more or even all temporary restorations are replaced with scan bodies, and a second intraoral scan is performed. Scan bodies are known in the art and have already been described above with respect to the method according to FIG. 2.

In a third step, an intraoral scan of the left side of the mouth cavity with 50% of temporary restorations in place is performed, i.e. a scan of 50% tissue and 50% temporary restorations is performed.

In a fourth step, an intraoral scan of the right side of the mouth cavity with 50% of temporary restorations in place is performed, i.e. a scan of 50% tissue and 50% temporary restorations is performed.

The thus obtained data are transmitted by usual means (e.g. a cable connection, a network connection, WLAN etc.) to a processing device, such as a computer. According to the DSSC concept, said processing device is located at a dental service center as described above. In said dental service center, a final restoration is designed and manufactured as described above for the other dental appliances and temporary restoration.

The thus produced final restoration is transferred back to the clinical center by usual means such as mail, airmail, or a courier. In the clinical center, the final restoration is placed into the mouth cavity of the person according to a conventional process known in the art. The person is now provided with the desired final restoration.

Figure 6:
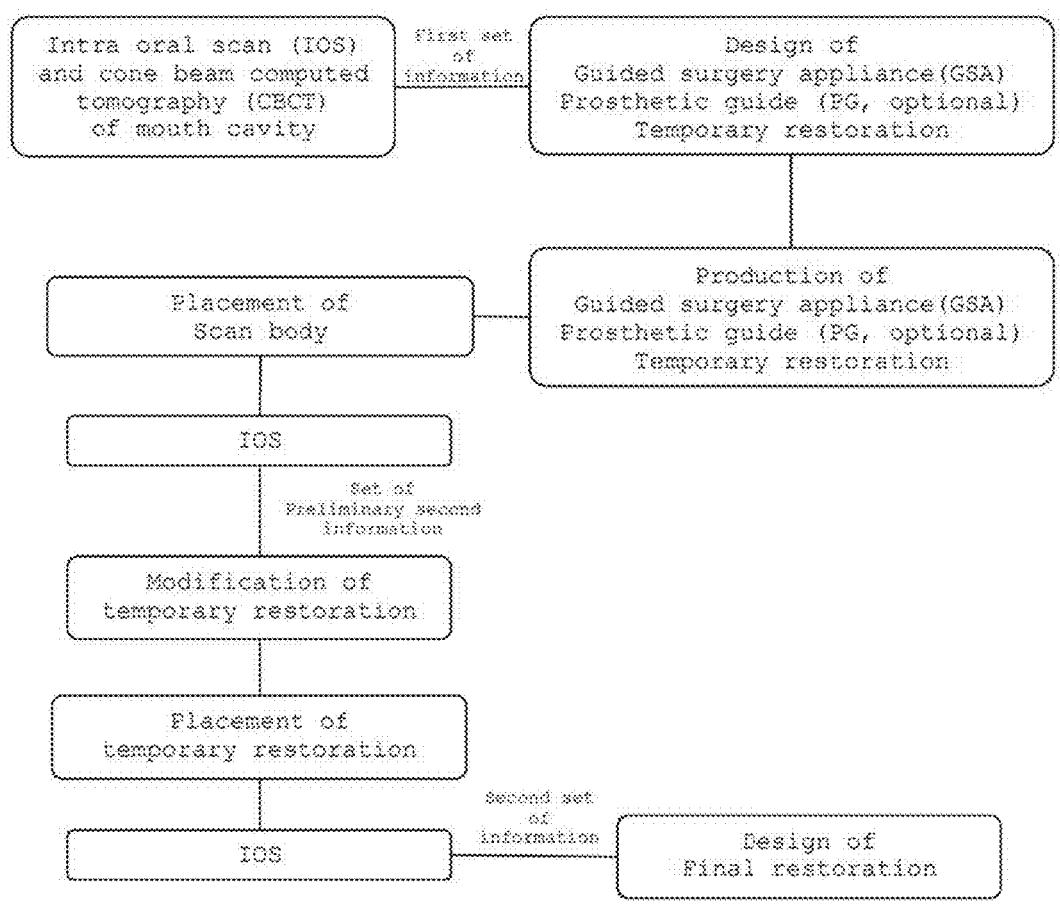
FIG. 6 is a flow-chart of the production of an implant-supported partially edentulous screw-retained prosthesis according to the DSCS (Dentaswiss clinical center) concept.

In FIG. 6, the manufacture of an implant supported partially edentulous screw-retained prosthesis according to the DSCS concept is illustrated. Said method comprises the steps of:
a) generating a first set of digital information of the mouth cavity of a person;
b) providing a temporary restoration with the aid of said first set of digital information,
c) generating a set of preliminary second information with at least one scan body, preferably a plurality of scan bodies corresponding to the number of provided implants, being within said mouth cavity,
d) modifying said temporary restoration with the aid of said set of preliminary second information before being placed into the mouth cavity,
e) generating a second set of digital information of said mouth cavity with said temporary restoration being within said mouth cavity; and
f) providing a final restoration with the aid of said second set of digital information generated with said temporary restoration being within said mouth cavity.

The person to be provided with a final restoration is located at a clinical center for treatment. The clinical center may be, for example, a dentist's office, a hospital or another location where dental surgery may be carried out.

In the clinical center, information related to the mouth cavity is collected, as will be outlined in more detail below. For said purpose the clinical center is equipped with a device for generating said information, for example with an intraoral scanner (IOS) and/or a cone beam computed tomography device (CBCT).

Intraoral scanning is known in the art. Intraoral scanning can be performed with a camera including any sensor or sensors capable of acquiring image data representative of a person's mouth cavity, in particular its dental dentition. The camera may be a charge-coupled device (CCD) camera or a sensor capable of acquiring different dimensions (e.g., two-dimensional and three-dimensional views) of data representative of a dentition. The camera can include an intra-oral 3D camera (104) configured to acquire 3D surface geometry data representative of the person's dentition. An example of a suitable camera is a 3D Rainbow camera configured to acquire images using techniques described in U.S. Pat. Nos. 5,675,407, 6,028,672, and 6,147,760. Another example is the TRIOS® technology of 3shape, which allows powder-free scanning and on-screen visualization of the digital impression taken.

In addition to the digital impression obtained by intraoral scanning, according to the present invention preferably further information is collected by an X-ray technology. Preferably, the X-ray technology is cone beam computed tomography (CBCT). CBCT is known in the art and is useful for determining anatomical parameters such as bone density and tooth root orientation. According to the present invention, by combining a digital impression technology such as intraoral scanning with a X ray technology such as CBCT, a first set of digital information is generated which is suitable for accurately designing dental appliances and temporary or final restorations.

In a next step, the thus obtained first set of digital information is used for designing a temporary restoration and optionally one or more dental appliances. Preferably, the first set of digital information is transmitted by usual means (e.g. a cable connection, a network connection, WLAN etc.) to a processing device, such as a computer. According to the DSCS concept, said processing device is located at a dental service center. The dental service center may be, for example, the laboratory of a dental technician, or another location where design and production of dental appliances and temporary and final restorations may be carried out. The dental service center may be at a completely distant location than the clinical center, but may also be situated in the same building, e.g. in a hospital.

According to a preferred embodiment, the dental service center may be a centralized center where a plurality of skilled persons, such as dental technicians, provides their services to a plurality of clinical centers, thus giving rise to synergistic effects. One or several of such centralized centers may be provided.

The dental service center is equipped with processing units, such as computers, for processing the information obtained from the clinical center, and for designing dental appliances and temporary and final restorations.

Preferably, the first set of information is transmitted to the processing unit in the form of a DICOM file. DICOM (Digital imaging and communication in medicine) is an open standard for storing and exchanging information in the medicinal area, including image information. DICOM is known in the art and used frequently in medicinal equipment. Providing digital information in the form of a DICOM file thus ensures interoperability between different devices.

With said first set of information, several different dental appliances as well as a temporary restoration may now be designed and produced. The design and production of those additional components is preferably performed in the same manner as described above with respect to the method of FIG. 2. Reference is made to the respective disclosure.

In detail, according to the method of FIG. 6, in said step preferably a guided surgery appliance, an optional prosthetic guide and a temporary restoration are designed and produced.

A guided surgery appliance has already been described above with respect to the method according to FIG. 2. Reference is made to the respective disclosure above.

In the method of the present invention, a customized guided surgery appliance to fit onto the mucosa of the upper or lower jaw bone of the person to be provided with a prosthesis, is designed and produced with the aid of said second set of information collected as described above. Preferably, said guided surgery appliance is prepared with a stereolithographic (3D) printer.

It should be explicitly mentioned that the present invention is not related to the step of drilling borings within the jaw bones of a person and providing implants within said borings. The method of the present invention merely provides tools for such an operation, such as the above mentioned guided surgery appliance.

In the method according to FIG. 6, the temporary restoration is supported by implants. According to the present invention, any commonly used implant may be employed. As mentioned above, and outside the scope of this invention, the implants are provided within the mouth cavity with the aid of the above mentioned guided surgery appliance. In an optional next step, abutments may be provided in the implants. Typically, conventionally used abutments such as multi-use abutments (MUA) are screwed into the implants. This can be done in a conventional manner by the dentist without any appliance.

According to a preferred embodiment of said optional method of the present invention, however, a prosthetic guide is provided as an additional dental appliance. A suitable prosthetic guide has already been described above with respect to the method according to FIG. 2. Reference is made to the respective disclosure above. Preferably, an embodiment of a prosthetic guide as shown in FIG. 10 may be used.

The thus produced dental appliances are transferred back to the clinical center by usual means such as mail, airmail, or a courier.

In the clinical center, with the aid of the above described guided surgery appliance borings for the implants are drilled and the implants are provided in the mouth cavity in an otherwise conventional manner. Subsequently, optionally with the aid of the prosthetic guide abutments are placed into the implants.

In contrast to the method of FIG. 5, in the method of FIG. 6 according to the DSCS concept a modification of the temporary restoration is performed at the clinical center.

For that purpose, additional information on the mouth cavity is collected. Said additional information is referred to as a set of preliminary second information. According to a preferred embodiment, said set of preliminary second information is obtained by providing one or more scan bodies in the mouth cavity, and an intraoral scan is performed. Scan bodies are known in the art and have already been described above with respect to the method of FIG. 2.

According to the DSCS concept described in FIG. 6, the clinical center is also provided with a processing unit for designing a temporary restoration, as well as with a manufacturing unit for producing a temporary restoration. Suitable processing units and manufacturing units have already been described above with respect to the method of FIG. 2. Reference is made to the disclosure above.

Similar to the design and production of a temporary restoration in a dental service center according to the method of FIG. 2, in the method according to FIG. 6 the pre-designed temporary restoration from the dental service center is now re-designed with the aid of the set of preliminary second information. The re-design is performed at the clinical center with the aid of a processing unit comprising respective software as described above. The re-designed temporary restoration is subsequently produced with a manufacturing unit provided at the clinical center, such as a CNC (computer numeric controlled) device, for example a CNC milling machine, or a 3D printer, such as a stereolithographic printer.

Optionally, a cap such as a conical sleeve may now be placed on optionally inserted abutments. Finally, the temporary restorations designed and manufactured in the dental service center are provided. Those steps are conventionally performed in dental surgery and not in the scope of the present invention.

The thus provided temporary restoration is allowed to heal, usually for a period of four weeks to three months. It is understood, however, that the healing period may vary from person to person.

After the healing period is finalized, the final restoration is manufactured and placed into the person's mouth cavity. For that purpose, a third set of digital information is obtained from the person's mouth cavity. Said collection of information is performed as already discussed above with respect to the gathering of the first set of information, preferably by intraoral scanning.

According to a preferred embodiment of the present invention, in order to obtain as many information as possible, a sequence of four intraoral scan steps is performed at this stage:

In a first step, the mouth cavity with the provided temporary restorations is scanned.

In a second step, one or more or even all temporary restorations are replaced with scan bodies, and a second intraoral scan is performed. Scan bodies are known in the art and have already been described above with respect to the method according to FIG. 2.

In a third step, an intraoral scan of the left side of the mouth cavity with 50% of temporary restorations in place is performed, i.e. a scan of 50% tissue and 50% temporary restorations is performed.

In a fourth step, an intraoral scan of the right side of the mouth cavity with 50% of temporary restorations in place is performed, i.e. a scan of 50% tissue and 50% temporary restorations is performed.

The thus obtained data are transmitted by usual means (e.g. a cable connection, a network connection, WLAN etc.) to a processing device, such as a computer. According to the DSSC concept, said processing device is located at a dental service center as described above. In said dental service center, a final restoration is designed and manufactured as described above for the other dental appliances and temporary restoration.

The thus produced final restoration is transferred back to the clinical center by usual means such as mail, airmail, or a courier. In the clinical center, the final restoration is placed into the mouth cavity of the person according to a conventional process known in the art. The person is now provided with the desired final restoration.

Next, a method of providing a full denture edentulous prosthesis will be described in detail.

Figure 7:
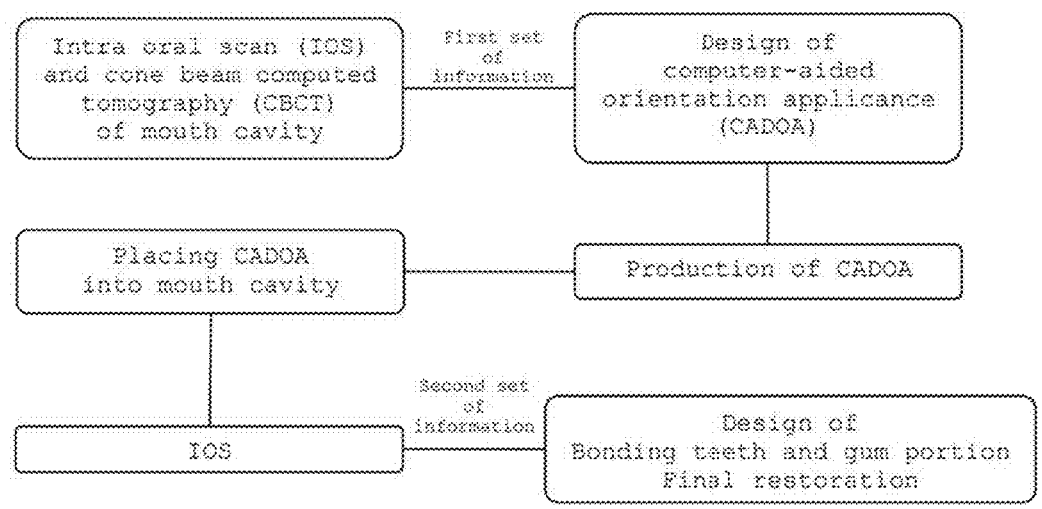
FIG. 7 is a flow-chart of the production of a full denture edentulous prosthesis according to the DSSC (Dentaswiss service center) concept.

In FIG. 7, the manufacture of a full denture edentulous prosthesis according to the DSSC concept is illustrated. Said method comprises the steps of:
- a) generating a first set of digital information of the mouth cavity of a person;
- b) providing an orientation appliance with the aid of said first set of digital information;
- c) generating a second set of digital information of said mouth cavity with said orientation appliance being within said mouth cavity,
- d) providing a final restoration with the aid of said second set of digital information generated with said temporary restoration being within said mouth cavity.

The person to be provided with a final restoration is located at a clinical center for treatment. The clinical center may be, for example, a dentist's office, a hospital or another location where dental surgery may be carried out.

In the clinical center, information related to the mouth cavity is collected, as will be outlined in more detail below. For said purpose the clinical center is equipped with a device for generating said information, for example with an intraoral scanner (IOS) and/or a cone beam computed tomography device (CBCT).

Intraoral scanning is known in the art. Intraoral scanning can be performed with a camera including any sensor or sensors capable of acquiring image data representative of a person's mouth cavity, in particular its dental dentition. The camera may be a charge-coupled device (CCD) camera or a sensor capable of acquiring different dimensions (e.g., two-dimensional and three-dimensional views) of data representative of a dentition. The camera can include an intra-oral 3D camera (104) configured to acquire 3D surface geometry data representative of the person's dentition. An example of a suitable camera is a 3D Rainbow camera configured to acquire images using techniques described in U.S. Pat. Nos. 5,675,407, 6,028,672, and 6,147,760. Another example is the TRIOS® technology of 3shape, which allows powder-free scanning and on-screen visualization of the digital impression taken.

In addition to the digital impression obtained by intraoral scanning, according to the present invention preferably further information is collected by an X-ray technology. Preferably, the X-ray technology is cone beam computed tomography (CBCT). CBCT is known in the art and is useful for determining anatomical parameters such as bone density and tooth root orientation. According to the present invention, by combining a digital impression technology such as intraoral scanning with a X ray technology such as CBCT, a first set of digital information is generated which is suitable for accurately designing dental appliances and temporary or final restorations.

In a next step, the thus obtained first set of digital information is used for designing an orientation appliance. Preferably, the first set of digital information is transmitted by usual means (e.g. a cable connection, a network connection, WLAN etc.) to a processing device, such as a computer.

According to the DSSC concept, said processing device is located at a dental service center. The dental service center may be, for example, the laboratory of a dental technician, or another location where design and production of dental appliances and temporary and final restorations may be carried out. The dental service center may be at a completely distant location than the clinical center, but may also be situated in the same building, e.g. in a hospital.

According to a preferred embodiment, the dental service center may be a centralized center where a plurality of skilled persons, such as dental technicians, provides their services to a plurality of clinical centers, thus giving rise to synergistic effects. One or several of such centralized centers may be provided.

The dental service center is equipped with processing units, such as computers, for processing the information obtained from the clinical center, and for designing dental appliances and temporary and final restorations.

Preferably, the first set of information is transmitted to the processing unit in the form of a DICOM file. DICOM (Digital imaging and communication in medicine) is an open standard for storing and exchanging information in the medicinal area, including image information. DICOM is known in the art and used frequently in medicinal equipment. Providing digital information in the form of a DICOM file thus ensures interoperability between different devices.

According to the method described in FIG. 7, in a next step an orientation appliance is designed and provided, as described above with respect to the method of FIG. 2. Preferably, in the method of FIG. 7 an embodiment of an orientation appliance according to FIGS. 8 and 9 is designed, manufactured and used.

As described above, the dimensions of the orientation appliance (1), including any part of said orientation appliance (1), are defined by the first set of information collected as described above. Thus, the orientation appliance (1) is designed and subsequently produced in a customized manner, i.e. it fits exactly to the person to be provided with a final restoration. This is achieved using design software known in the related field, such as the design software from DentaSwiss.

The orientation appliance (1) is manufactured by at least one manufacturing unit which is operated according to the design generated by the at least one processing unit. For example, the manufacturing unit may be a CNC (computer numeric controlled) device, such as a CNC milling machine. Alternatively, the manufacturing unit may be a 3D printer, such as a stereolithographic printer. It is understood, however, that any other software-controlled manufacturing unit commonly used for said purpose may be equally employed.

The orientation appliance (1) may be made from materials such as polymers as one single piece or in separate pieces which are subsequently connected with each other, as described above. The manufacture of such devices is generally known in the art and need not be discussed in detail here.

The thus produced orientation appliance is transferred back to the clinical center by usual means such as mail, airmail, or a courier.

In the clinical center, the orientation appliance is placed into the mouth cavity of the person. The orientation appliance is correctly adjusted within the mouth cavity. In the case of the embodiment of the orientation appliance (1) according to FIGS. 8 and 9, for example the distance between upper portion (2) and lower portion (3) and the position of the teeth (9*a*, 9*b*) is adjusted.

After adjustment, in the clinical center, information related to the mouth cavity is collected with the orientation appliance being adjusted within the mouth cavity. Said collection of information is performed as already discussed above with respect to the gathering of the first set of information, preferably by intraoral scanning.

Since said second set of information has been collected with the orientation appliance in place in the mouth cavity, it comprises additional valuable information, such as a reference point for setting up teeth as well as information on parameters such as VOD (vertical dimension of occlusion), centric relation (CR), centric occlusion (CO), esthetic parameters, phonetics and function of the final restoration.

Preferably, the second set of digital information is transmitted by usual means (e.g. a cable connection, a network connection or WLAN) to a processing device, such as a computer. According to the DSCS concept, said processing device is located at the dental service center described above.

Preferably, the second set of information is also transmitted to the processing unit in the form of a DICOM file, as described above with respect to the first set of information.

In the dental service center, with the aid of said second set of information now the desired final restoration in the form of a denture is designed and manufactured as described above for the other dental appliances and temporary restoration. Such final restorations are known in the art and not discussed here in detail.

The thus produced final restoration is transferred back to the clinical center by usual means such as mail, airmail, or a courier. In the clinical center, the final restoration is placed into the mouth cavity of the person according to a conventional process known in the art. The person is now provided with the desired final restoration.

The present invention is furthermore related to a system, preferably for performing any of the methods described above, comprising at least one device for generating information related to a mouth cavity of a person, at least one processing unit for performing operations of processing information obtained from said at least one device for generating information related to a mouth cavity of a person, and for designing, with the aid of said processed information, at least one component selected from the group consisting of an orientation appliance, a guided surgery appliance, a prosthetic guide, a temporary restoration and a final restoration, at least one manufacturing unit for providing, based on the design generated by the processing unit, at least one component selected from the group consisting of an orientation appliance, a guided surgery appliance, a prosthetic guide, a temporary restoration and a final restoration, and at least one component selected from the group consisting of an orientation appliance, a guided surgery appliance, a prosthetic guide, and a temporary restoration.

The device of generating information has already been described above. Preferably, said device for generating said information, for example with an intraoral scanner (IOS) and/or a cone beam computed tomography device (CBCT).

Intraoral scanning is known in the art. Intraoral scanning can be performed with a camera including any sensor or sensors capable of acquiring image data representative of a person's mouth cavity, in particular its dental dentition. The camera may be a charge-coupled device (CCD) camera or a sensor capable of acquiring different dimensions (e.g., two-dimensional and three-dimensional views) of data representative of a dentition. The camera can include an intra-oral 3D camera (104) configured to acquire 3D surface geometry data representative of the person's dentition. An example of a suitable camera is a 3D Rainbow camera configured to acquire images using techniques described in U.S. Pat. Nos. 5,675,407, 6,028,672, and 6,147,760. Another example is the TRIOS® technology of 3shape, which allows powder-free scanning and on-screen visualization of the digital impression taken.

In addition to the digital impression obtained by intraoral scanning, according to the present invention the system furthermore preferably comprises a device based on X-ray technology. Preferably, said device is a cone beam computed tomography (CBCT). CBCT is known in the art and is useful for determining anatomical parameters such as bone density and tooth root orientation. According to the present invention, by combining a digital impression technology such as intraoral scanning with a X ray technology such as CBCT, a first set of digital information is generated which is suitable for accurately designing dental appliances and temporary or final restorations.

The processing unit has already been described above. For example, processing units such as computers are used.

Digital information is transmitted from the device for generating information to said processing device by usual means (e.g. a cable connection, a network connection, WLAN etc.).

Said manufacturing unit has already been described above. Said manufacturing unit is a unit which is operated according to the design generated by the at least one processing unit. For example, the manufacturing unit may be a CNC (computer numeric controlled) device, such as a CNC milling machine. Alternatively, the manufacturing unit may be a stereolithographic (3D) printer. It is understood, however, that any other software-controlled manufacturing unit commonly used for said purpose may be equally employed.

Said at least one component selected from the group consisting of an orientation appliance, a guided surgery appliance, a prosthetic guide, and a temporary restoration, has already been described above. Those components are customized, i.e. they have been designed to fit exactly to the person to be provided with a prosthesis. The design and manufacture of the components is preferably performed as described above with any of the methods according to FIGS. 2 to 7.

Particularly preferred components to be used in the system of the present invention are the orientation appliance and/or the prosthetic guide as described above. A particularly preferred embodiment of an orientation appliance is shown In FIGS. 8 and 9. A particularly preferred embodiment of a prosthetic guide is shown in FIG. 10. Reference is made to the respective explanations of FIGS. 8 to 10 above.

According to the present invention, the various parts of said system do not have to be provided at the same location. According to a preferred embodiment of the present invention, the device for generating information related to a mouth cavity of a person is located at the clinical site where the person is provided with tooth restoration, whereas the processing unit and the manufacturing unit are provided at a dental service center. In said embodiment, the components manufactured in the dental service center are transferred to the clinical site.

According to another embodiment of the present invention, another manufacturing unit is also located at the clinical site.

Those embodiments have been described above in detail. Reference is made to the respective disclosure above.

The present invention is furthermore related to the use of an orientation appliance for denture restoration, preferably in a method for making implant supported full edentulous screw-retained prostheses, implant supported full edentulous cement-retained prostheses, and full denture-edentulous prostheses, wherein said orientation appliance comprises
- an upper portion and a lower portion, wherein said upper and lower portion are adapted to the dimensions of a mouth cavity of a person,
- wherein said upper and lower portion are connected via a movable part for adjusting the distance between said upper and lower portion,
- wherein at least one, preferably both, of said upper and lower portion comprises at least one radiopaque marker, preferably a plurality of radiopaque markers corresponding to the number of implants to be provided, for defining the position of an implant to be provided within the mouth cavity of the person, and
- wherein at least one of said upper and lower portion, preferably the upper portion, comprises at least one artificial tooth, preferably two artificial teeth which can be moved with respect to each other, said artificial tooth being movably linked to said upper or lower portion.

The present invention is furthermore related to the use of a prosthetic guide for denture restoration, preferably in a method for making implant supported full edentulous screw-retained prostheses, implant supported full edentulous cement-retained prostheses, implant supported partially edentulous screw-retained prostheses, and full denture-edentulous prostheses, wherein said prosthetic guide comprises
- a body adapted to the dimensions of the mouth cavity of a person,
- at least one opening, preferably a plurality of openings corresponding to the number of provided implants, adapted for inserting an abutment through the opening into an implant provided in the mouth cavity of the person, and
- preferably at least one abutment, preferably a plurality of abutments corresponding to the number of provided implants, provided in said at least one opening.

The present invention is furthermore related to the use of a system for denture restoration, preferably in a method for making implant supported full edentulous screw-retained prostheses, implant supported full edentulous cement-retained prostheses, implant supported partially edentulous screw-retained prostheses, and full denture-edentulous prostheses, said system comprising
- at least one device for generating information related to a mouth cavity of a person,
- at least one processing unit for performing operations of processing information obtained from said at least one device for generating information related to a mouth cavity of a person, and for designing, with the aid of said processed information, at least one component selected from the group consisting of an orientation appliance, a guided surgery appliance, a prosthetic guide, a temporary restoration and a final restoration,
- at least one manufacturing unit for providing, based on the design generated by the processing unit, at least one component selected from the group consisting of an orientation appliance, a guided surgery appliance, a prosthetic guide, a temporary restoration and a final restoration, and
- at least one component selected from the group consisting of an orientation appliance, a guided surgery appliance, a prosthetic guide, and a temporary restoration.

The present invention is furthermore related to a method of generating digital information on the mouth cavity of a person to be provided with denture restoration, preferably selected form the group consisting of implant supported full edentulous screw-retained prostheses, implant supported full edentulous cement-retained prostheses, and full denture-edentulous prostheses, comprising the step of placing an orientation appliance as described above into the mouth cavity and generating a set of digital information of said mouth cavity.

The present invention is furthermore related to a method of inserting at least one abutment, preferably a plurality of abutments corresponding to the number of provided implants, into an implant provided in the mouth cavity of a person, comprising the step of placing a prosthetic guide as described above into the mouth cavity, wherein said prosthetic guide is provided with at least one abutment, preferably a plurality of abutments corresponding to the number of provided implants, and inserting said at least one abutment into the implant.

What is claimed is:

1. A method for denture restoration, the method comprising:
   a) generating a first set of digital information of a mouth cavity of a patient;
   b) producing an orientation appliance from said first set of digital information, the orientation appliance comprising upper and lower portions that are adapted to a size and shape of the mouth cavity of the patient, and a movable part facilitates adjusting a position of the upper portion relative to the lower portion, and, thereafter, placing the orientation appliance in the mouth cavity of the patient;
   c) generating a second set of digital information of said mouth cavity with said orientation appliance being placed within said mouth cavity of the patient;
   d) producing a temporary restoration using said second set of digital information;
   e) placing said temporary restoration within said mouth cavity of the patient and generating a third set of digital information of said mouth cavity with said temporary restoration, provided in step d), being placed within said mouth cavity of the patient; and
   f) producing a final restoration using
      said third set of digital information generated with said temporary restoration being placed within said mouth cavity of the patient.

2. The method according to claim 1, wherein said first set of information is generated by a combination of intraoral scanning and cone beam computed tomography.

3. The method according to claim 1, wherein in step b) the temporary restoration is produced in order to obtain the final restoration selected from the group of implant supported partially edentulous screw-retained prostheses.

4. The method according to claim 1, wherein before a set of information is generated with the temporary restoration being placed within said mouth cavity, a set of preliminary second or third information is generated, and said temporary restoration is modified with the aid of said set of preliminary second or third information before being placed into the mouth cavity.

5. The method according to claim 4, wherein said second and third sets of processing information are generated with intraoral scanning with the aid of a scan body.

6. The method according to claim 1, wherein in step d) in addition to said temporary restoration, a dental appliance selected from the group consisting of a guided surgery appliance, a prosthetic guide, and a combination thereof, is also produced with the aid of said second set of digital information.

7. The method according to claim 1, wherein said third set of information and said second set of information are generated with intraoral scanning with the aid of a scan body.

8. The method according to claim 1, wherein at least one of the upper and the lower portions comprises at least one radiopaque reference.

9. A system for performing a denture restoration for a patient, the system comprising:
 at least one device for generating digital information related to a mouth cavity of the patient,
 at least one processing unit for performing at least first and second operations of processing information obtained from said at least one device for generating information related to the mouth cavity of the patient, and for first producing, using the first processed information, an orientation appliance and, thereafter, placing the produced orientation appliance in the mouth cavity and generating a second set of processing information of the mouth cavity with said orientation appliance placed within the mouth cavity of the patient, and the second processed information being used for generating one of a temporary restoration and a final restoration,
 at least one manufacturing unit for providing, based on the design generated by the processing unit, the final restoration and at least the orientation appliance, and
 at least one component selected from the group consisting of the orientation appliance, a guided surgery appliance, a prosthetic guide, and the temporary restoration.

10. The system according to claim 9, wherein said device for generating information related to the mouth cavity of the patient is an intraoral scanner, a cone beam computed tomography device, or a combination thereof.

11. The system according to claim 9, wherein said manufacturing unit is a 3D printer or a CNC device.

12. The system according to claim 9, wherein said device for generating information is provided at a different location than the processing unit and the manufacturing unit.

13. The system according to claim 9, wherein said processing unit is provided at a different location than the device for generating information and the manufacturing unit.

14. A method for denture restoration, the method comprising:
 a) generating a first set of digital information of a mouth cavity of a patient;
 b) producing an orientation appliance from the first set of digital information, the orientation appliance comprising upper portion and a lower portion that are adapted to a size and shape of the mouth cavity of the patient, and a movable part facilitates adjusting a position of the upper portion relative to the lower portion, and, thereafter, placing the orientation appliance in the mouth cavity of the patient;
 c) generating a second set of digital information of said mouth cavity with said orientation appliance being placed within said mouth cavity of the patient; and
 d) producing a final restoration using said second set of digital information generated with said orientation appliance being placed within said mouth cavity;
 wherein the final restoration is selected from the group of implant supported full edentulous screw-retained prostheses, implant supported full edentulous cement-retained prostheses, and full denture-edentulous prostheses.

15. A method for preparing a final restoration for a patient, the method comprising:
 a) generating a first set of digital information of a mouth cavity of the patient;
 b) using the first set of digital information to produce an orientation appliance;
 c) placing the orientation appliance in the mouth cavity of the patient and generating a second set of digital information of the mouth cavity with the orientation appliance located within the mouth cavity;
 d) using the second set of digital information to produce a temporary restoration;
 e) placing the temporary restoration within the mouth cavity of the patient and generating a third set of digital information of the mouth cavity with the temporary restoration located within the mouth cavity of the patient; and
 f) using the third set of digital information, generated with the temporary restoration located within the mouth cavity of the patient, to produce the final restoration.

* * * * *